(12) United States Patent
Branton et al.

(10) Patent No.: US 10,228,348 B2
(45) Date of Patent: *Mar. 12, 2019

(54) MOLECULAR CHARACTERIZATION DEVICE

(71) Applicant: President and Fellows of Harvard College, Cambridge, MA (US)

(72) Inventors: Daniel Branton, Lexington, MA (US); Jene A Golovchenko, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 178 days.

This patent is subject to a terminal disclaimer.

(21) Appl. No.: 15/004,248

(22) Filed: Jan. 22, 2016

(65) Prior Publication Data

US 2016/0139079 A1 May 19, 2016

Related U.S. Application Data

(63) Continuation of application No. 13/040,537, filed on Mar. 4, 2011, now Pat. No. 9,274,097, which is a continuation of application No. 12/214,016, filed on Jun. 16, 2008, now abandoned, which is a continuation of application No. 11/399,663, filed on Apr. 6, 2006, now Pat. No. 7,468,271.

(60) Provisional application No. 60/668,632, filed on Apr. 6, 2005, provisional application No. 60/688,799, filed on Jun. 9, 2005, provisional application No. 60/727,603, filed on Oct. 18, 2005.

(51) Int. Cl.
| | |
|---|---|
| *G01N 27/447* | (2006.01) |
| *C12Q 1/6869* | (2018.01) |
| *G01N 33/487* | (2006.01) |
| *B82Y 15/00* | (2011.01) |

(52) U.S. Cl.
CPC ..... *G01N 27/44791* (2013.01); *C12Q 1/6869* (2013.01); *G01N 27/44743* (2013.01); *G01N 33/48721* (2013.01); *B82Y 15/00* (2013.01); *Y10S 977/762* (2013.01)

(58) Field of Classification Search
None
See application file for complete search history.

(56) References Cited

U.S. PATENT DOCUMENTS

| | | | |
|---|---|---|---|
| 5,795,782 A * | 8/1998 | Church | C07K 14/705 435/4 |
| 6,413,792 B1 | 7/2002 | Sauer et al. | |
| 6,627,067 B1 | 9/2003 | Branton et al. | |
| 6,870,361 B2 | 3/2005 | Chopra et al. | |
| 7,005,264 B2 | 2/2006 | Su et al. | |
| 7,466,069 B2 | 12/2008 | Golovchenko et al. | |
| 7,468,271 B2 * | 12/2008 | Golovchenko | C12Q 1/6869 435/287.2 |
| 7,744,816 B2 * | 6/2010 | Su | G01N 33/6803 422/68.1 |
| 7,803,607 B2 * | 9/2010 | Branton | C12Q 1/6869 435/287.2 |
| 8,092,697 B2 * | 1/2012 | Branton | C12Q 1/6869 216/19 |
| 8,206,568 B2 | 6/2012 | Branton et al. | |
| 8,273,532 B2 | 9/2012 | Gershow et al. | |
| 8,864,969 B2 * | 10/2014 | Liu | G01N 33/48721 204/452 |
| 8,986,928 B2 * | 3/2015 | Turner | C12Q 1/6869 435/6.1 |
| 9,274,097 B2 * | 3/2016 | Golovchenko | C12Q 1/6869 |
| 9,696,277 B2 * | 7/2017 | Dunbar | G01N 33/48721 |
| 2004/0038260 A1 | 2/2004 | Martin et al. | |

FOREIGN PATENT DOCUMENTS

| | | |
|---|---|---|
| EP | 1443318 A1 | 4/2004 |
| EP | 1441213 A1 | 7/2004 |
| WO | 2004028673 A1 | 4/2004 |

(Continued)

OTHER PUBLICATIONS

Kasianowicz et al., "Characterization of individual polynucleotide molecules using a membrane channel," Proc. Natl. Acad. Sci. USA, vol. 93, pp. 13770-13773, Nov. 1996.

Desai et al., "Characterization of micromachined silicon membranes for immunoisolation and bioseparation applications," Jnl. of Membrance Science, vol. 159, pp. 221-231, 1999.

Deamer et al., "Nanopores and nucleic acids: prospects for ultrarapid sequencing," TIBTECH, vol. 18, pp. 147-151. Apr. 2000.

Siwy et al., "Rectification and voltage gating of ion curents in a nanofabricated pore," Europhys. Lett., vol. 60, pp. 349-355, ABST. Nov. 2002.

(Continued)

*Primary Examiner* — Ann Y Lam
(74) *Attorney, Agent, or Firm* — Theresa A. Lober

(57) ABSTRACT

Provided is a solid state support structure including an aperture having a molecular entrance and a molecular exit. A first reservoir is in fluidic communication with the molecular entrance of the aperture and contains a molecule-bearing liquid solution. A second reservoir is in fluidic communication with the molecular exit of the aperture for containing a molecule-bearing liquid solution. A first liquid channel is connected to the first reservoir within less than about 300 microns of the aperture in the support structure and includes molecule-bearing liquid solution for delivery to the first reservoir. A second liquid channel is connected to the second reservoir for accepting molecule-bearing liquid solution from the second reservoir. An electrical connection between the first reservoir and the second reservoir imposes an electrical bias between the first reservoir and the second reservoir for driving the molecule-bearing liquid solution through the aperture in the solid state support structure.

14 Claims, 13 Drawing Sheets

(56) References Cited

FOREIGN PATENT DOCUMENTS

| WO | 2004035211 A1 | 4/2004 |
|---|---|---|
| WO | 2004077503 A1 | 9/2004 |

OTHER PUBLICATIONS

Deamer et al., "Characterization of Nucleic Acids by Nanopore Analysis," Acc. Chem. Res., vol. 35, No. 10, pp. 817-825, 2002.
Saleh et al., "An Artificial Nanopore for Molecular Sensing," NanoLetters, vol. 3, No. 1, pp. 37-38, Dec. 3, 2002.
Bates et al., "Dynamics of DNA Molecules in a Membrane Channel Probed by Active Control Techniques," Biophysical Jnl., vol. 84, pp. 2366-2372. Apr. 2003.
Storm et al., "Fabrication of solid-state nanopores with single-nanometre precision," Naure Materials, vol. 2, pp. 537-540, Aug. 2003.
Li et al., "DNA molecules and configurations in a solid-state nanopore microscope," Nature Materials, vol. 2, pp. 611-615, Sep. 2003.
Nakane et al., "Nanopore sensors for nucleic acid analysis," J. Phys.: Condens, Matter, vol. 15, pp. R1365-R1393, 2003.
Chang et al., "DNA-Mediated Fluctuations in Ionic Current through Silicon Oxide Nanopore Channels," Nano Letters, vol. 4, No. 8, pp. 1551-1556, Jul. 7, 2004.
Chen et al., "Probing Single DNA Molecule Transport Using Fabricated Nanopores," Nano Letters, vol. 4, No. 11, pp. 2293-2298, Oct. 26, 2004.
Fologea et al., "Detecting Single Stranded DNA with a Solid State Nanopore," Nano Letters, vol. 5, No. 10, pp. 1905-1909, Aug. 31, 2005.
European Patent Application 11004003.7, Extended European Search Report, pp. 1-2, Annex, Examination report, Sheets 1-4, dated Sep. 2011.
International Patent Application PCT/US2006/012800, International Search Report PCT/ISA/210 First sheet, second sheet pp. 1-2, continuation of first sheet pp. 1-2, patent family annex; Written Opinion of the International Searching Authority, PCT/ISA/237 Cover sheet, Boxes I, III, IV, and V, Separate sheet sheets 1-6, dated Jan. 2008.
Bates et al., "Dynamics of DNA Molecules in a Membrane Channel Probed by Active Control Techniques," Biophysical Journal, vol. 84, pp. 2366-2372, Apr. 2003.
Zheng et al., "Towards Single Molecule Manipulation with Dielectrophoresis Using Nanoelectrodes," 2003 Third IEEE Conf. on Nanotechnology, IEEE-NANO 2003, Proceedings, Cat. No. 03TH8700, vol. 2, pp. 437-440, 2003.
Branton et al., "Adapting to nanoscale events," Nature, vol. 398, pp. 660-661, Apr. 1999.
Meller et al., "Rapid nanopore discrimination between single polynucleotide molecules," PNAS, vol. 97, No. 3, pp. 1079-1084, Feb. 2000.
Meller et al., "Voltage-Driven DNA Translocations through a Nanopore," Phys. Rev. Letts., vol. 86, No. 15, pp. 3435-3438, Apr. 2001.
Wang et al., "Nanopores with a spark for single-molecule detection," Nature Biotechnology, vol. 19, pp. 622-623, Jul. 2001.
Nakane et al., "Evaluation of nanopores as candidates for electronic analyte detection," Electrophoresis, vol. 23, pp. 2592-2601, 2002.
Meller et al, "Single molecule measurements of DNA transport through a nanopore," Electrophoresis, vol. 23, pp. 2583-2591, 2002.
Meller, "Dynamics of polynucleotide transport through nanometre-scale pores," Journal of Physics: Condensed Matter, vol. 15, pp. R581-R607, 2003.
Sauer-Budge et al., "Unzipping Kinetics of Double-Stranded DNA in a Nanopore," Phys. Rev. Letts., vol. 90, No. 23, pp. 238101-1-238101-4, Jun. 2003.
Nakane et al., "A Nanosensor for Transmembrane Capture and Identification of Single Nucleic Acid Molecules," Biophysical Journal, vol. 87, pp. 615-621, Jul. 2004.
Chen et al., "Atomic Layer Deposition to Fine-Tune the Surface Properties and Diameters of Fabricated Nanopores," Nano Letters, vol. 4, No. 7, pp. 1333-1337, Jun. 2004.
Fologea et al., "Detecting Single Stranded DNA with a Solid State Nanopore," Nano Letters, vol. 5, No. 10, pp. 1905-1909, Aug. 2005.
Indian Patent Application No. 4607/CHENP/2007, First Examination Report, pp. 1-2, dated Sep. 2014.
Indian Patent Application No. 4607/CHENP/2007, response to India Patent Examination Report, Response pp. 1-6, claims pp. 63-68 dated Sep. 2015.

* cited by examiner

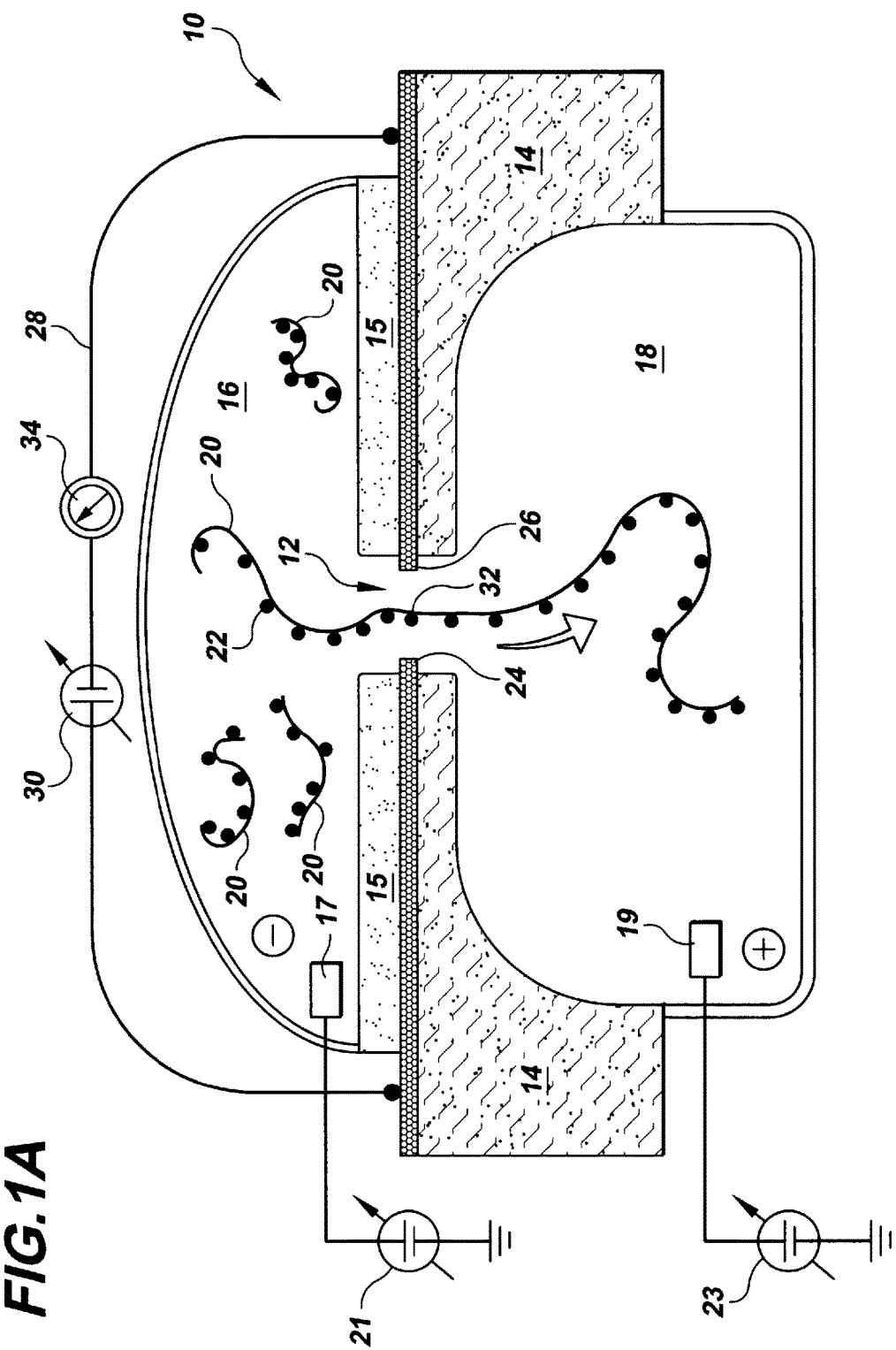

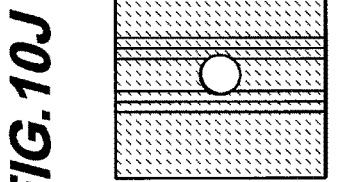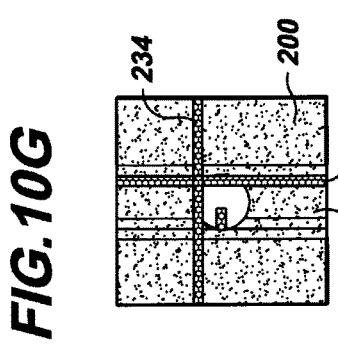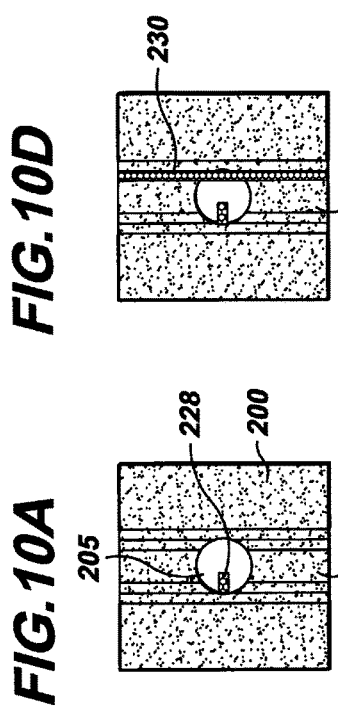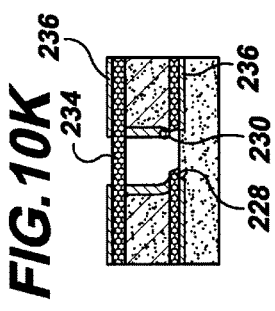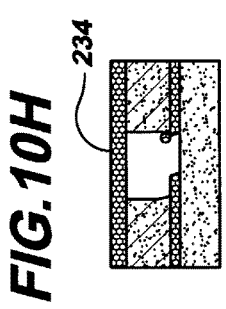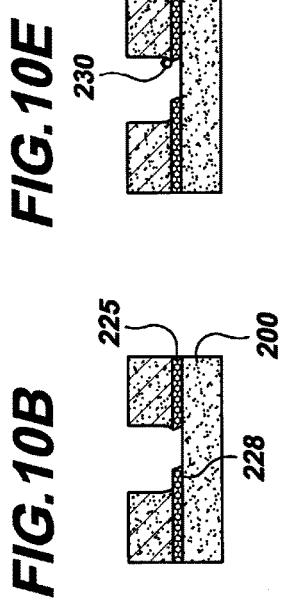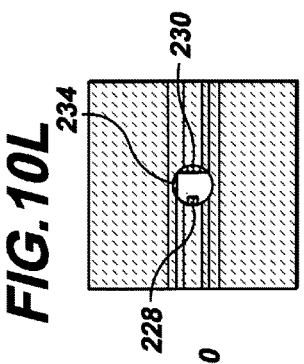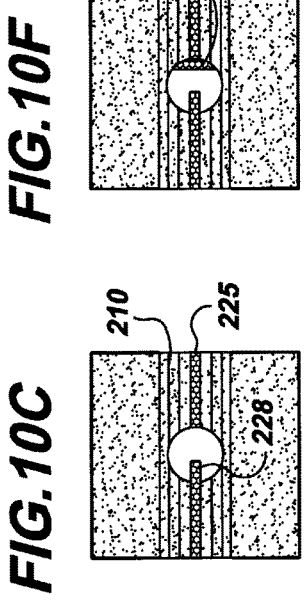

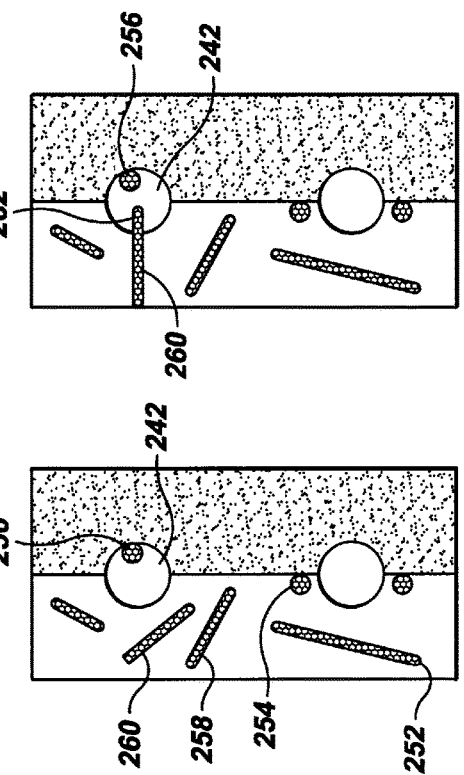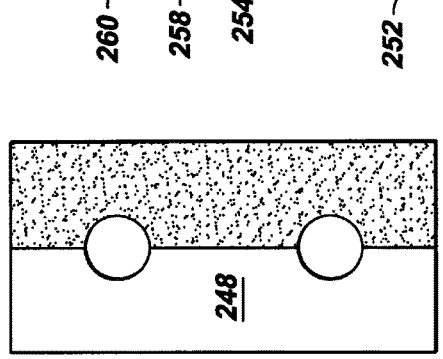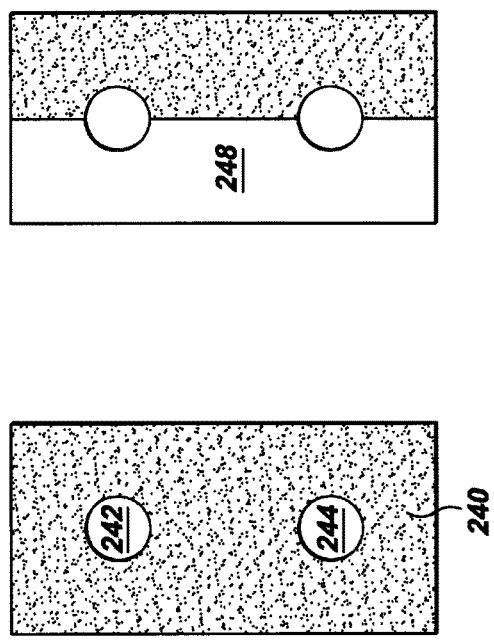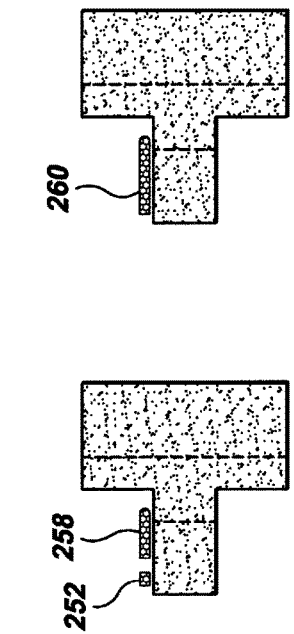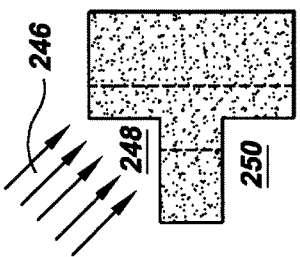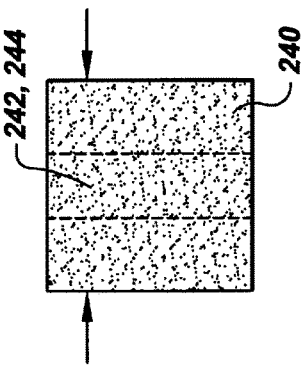

MOLECULAR CHARACTERIZATION DEVICE

CROSS-REFERENCE TO RELATED APPLICATIONS

This application is a continuation of U.S. application Ser. No. 13/040,537, filed Mar. 4, 2011, which in turn is a continuation of U.S. application Ser. No. 12/214,046, filed Jun. 16, 2008, now issued as U.S. Pat. No. 8,092,697, which in turn is a continuation of U.S. application Ser. No. 11/399,663, filed Apr. 6, 2006, U.S. Pat. No. 7,468,271, which claims the benefit of U.S. Provisional Application No. 60/668,632, filed Apr. 6, 2005 and U.S. Provisional Application No. 60/688,799, filed Jun. 9, 2005, and U.S. Provisional Application No. 60/727,603, filed Oct. 18, 2005, the entirety of all of which above-recited applications are hereby incorporated by reference.

STATEMENT REGARDING FEDERALLY SPONSORED RESEARCH

This invention was made with Government support under National Institute of Health grant "Electronic sequencing in nanopores" RO1HG003703. The Government has certain rights in the invention.

BACKGROUND

This invention relates generally to detection and identification of molecules, and more particularly relates to molecular analysis techniques for characterization and sequencing of polymers, including biopolymers such as polynucleotides.

The detection, characterization, identification, and sequencing of molecules, including biomolecules, e.g., polynucleotides such as the biopolymer nucleic acid molecules DNA, RNA, and peptide nucleic acid (PNA), as well as proteins, and other biological molecules, is an important and expanding field of research. There is currently a great need for processes that can determine the hybridization state, configuration, monomer stacking, and sequence of polymer molecules in a rapid, reliable, and inexpensive manner. Advances in polymer synthesis and fabrication and advances in biological development and medicine, particularly in the area of gene therapy, development of new pharmaceuticals, and matching of appropriate therapy to patient, are in large part dependent on such processes.

In one process for molecular analysis, it has been shown that molecules such as nucleic acids and proteins can be transported through a natural or synthetic nano-scale pore, or nanopore, and that characteristics of the molecule, including its identification, its state of hybridization, its interaction with other molecules, its sequence, i.e., the linear order of the monomers of which a polymer is composed, can be discerned by and during transport through the nanopore. Transport of a molecule through a nanopore can be accomplished by, e.g., electrophoresis, or other translocation mechanism.

If the dimensions of the nanopore are such that an extended nucleic acid molecule occupies a substantial fraction of the nanopore's cross-sectional area during translocation, the polymer molecule can be characterized by and during transport through the nanopore by at least two mechanisms. In a first of these, the translocating molecule transiently reduces or blocks the ionic current produced by application of a voltage between the two compartmentalized liquid ion-containing solutions in contact with each end of nanopore. In a second of these, the translocating molecule transiently alters the electron current, including the tunneling electron current, produced by applying a bias between two closely spaced local probes that are located to produce a nanoscale gap, either on apposed points on the perimeter of the nanopore or at opposite ends of a very short nanopore. Given that during its passage through the nanopore each nucleotide in the polymer produces a characteristically distinct modulation of the ionic current or the electron current, the resulting sequence of either the ionic or the electron current modulations can reflect the characteristics of the translocating polymer molecule.

Ideally, these molecular analysis techniques, like others that have been proposed, should enable molecular characterization with single monomer resolution. Unambiguous resolution of individual monomer characteristics is critical for reliable applications such as biomolecular sequencing applications. But this capability is difficult to achieve in practice, due to several aspects of molecular detection and analysis in general.

First, for any molecular orientation, the speed at which a molecule is characterized, e.g., the speed at which a sequence of nucleotides is detected, may impact the production of a useful molecular characterization signal. The ability to discern changes in a characterization signal or other indicator from one monomer to the next may be highly sensitive to the speed at which the nucleotides are characterized. For example, the speed at which a nucleotide is transported through a nanopore may impact the degree of ionic current blockage or electron current modulation caused by that nucleotide, or may exceed the bandwidth of the measurement instruments that can be fabricated to detect the very small pico- or nanoampere currents typical of ionic current measurements or tunneling current measurements in a nanopore.

Second, the physical orientation of a given nucleotide as it is characterized may impact the detection of characteristics of that nucleotide. This difficulty is particularly acute when modulations of the electron current between two closely spaced local probes, oriented to produce a nanoscale gap, are to be sensed. Such modulations in electron current, including tunneling current, between two closely spaced probes are known to be especially sensitive to atomic scale variation in the distance between the two probes or to the precise orientation of molecules between the two probes. Thus, e.g., each alternative nucleotide orientation within a DNA strand may produce a different detection and characterization signal or other indicator, and such signals may be ambiguous for multiple nucleotides or multiple molecular features. For example, the orientation of a nucleotide as it passes through a nanopore having a location-specific limiting asperity may alter the electronic current modulation caused by that nucleotide at the location of the asperity. Various nucleotides and various molecular attributes may result in similar, or indistinguishable electron current modulations, depending on their orientation as they are transported through a nanopore. These examples illustrate that, in general, the challenges of speed control and nano-scale spatial orientation limit the ability to achieve precise, high resolution molecular characterization such as biopolymer sequencing.

SUMMARY

The molecular characterization device provided herein overcomes the control difficulties of prior molecular characterization techniques. In one embodiment there is provided is a solid state support structure including an aperture having a molecular entrance and a molecular exit. A first reservoir is in fluidic communication with the molecular entrance of the aperture and contains a molecule-bearing liquid solution. A second reservoir is in fluidic communication with the molecular exit of the aperture for containing a molecule-bearing liquid solution. A first liquid channel is connected to the first reservoir within less than about 300 microns of the aperture in the support structure and includes molecule-bearing liquid solution for delivery to the first reservoir. A second liquid channel is connected to the second reservoir for accepting molecule-bearing liquid solution from the second reservoir. An electrical connection between the first reservoir and the second reservoir imposes an electrical bias between the first reservoir and the second reservoir for driving the molecule-bearing liquid solution through the aperture in the solid state support structure This device minimizes electrical capacitance for optimizing molecular characterization techniques, and enables a method in which a molecular translocation voltage can be applied across an aperture between a molecular inlet entrance and a molecular outlet exit for characterization of a molecule at the aperture. This molecular characterization device allows for fast, reliable, repeatable, and uncomplicated characterization of a wide range of molecules and molecular configurations. Other features and advantages of the device will be apparent from the following description and accompanying figures, and from the claims.

BRIEF DESCRIPTION OF THE DRAWINGS

FIG. 1A is a schematic cross-sectional view of a first example embodiment of a molecular characterization device provided by the invention, articulated with end-oriented carbon nanotube probes;

FIGS. 10A-10L are schematic cross-sectional views showing fabrication steps in a further example process for producing a molecular characterization device; and FIGS. 11A-11M are schematic cross-sectional views showing fabrication steps in a further example process for producing a molecular characterization device.

DETAILED DESCRIPTION

Figure 4A:
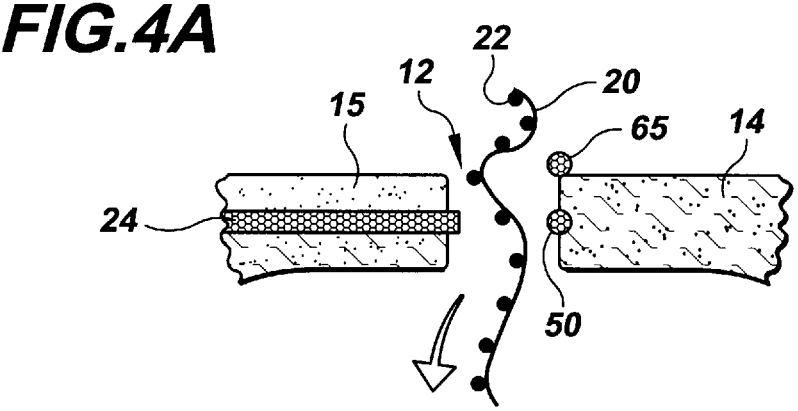
FIG. 4A is schematic cross-sectional view of a further example embodiment of a molecular characterization device provided by the invention, articulated with one end-oriented carbon nanotube probe, one side-oriented nanotube probe, and a side-oriented translocation control carbon nanotube.

Referring to FIG. 1A there is schematically shown a first example embodiment of a molecular characterization device 10 provided by the invention. For clarity of discussion, device features illustrated in FIG. 1 are not shown to scale. As shown in FIG. 1A, in the device there is provided a nano-scale aperture, or nanopore 12, in a support structure 14. On a first side of the support structure is a first liquid compartment 16, or reservoir, containing a liquid solution including molecules to be characterized, and on an opposite side of the support structure is a second liquid compartment 18, or reservoir into which characterized molecules are transported by translocation through the nanopore. A molecular entrance at the inlet to the aperture provides fluidic communication between the first reservoir 16 and the aperture, while a molecular exit at the outlet of the aperture provides fluidic communication between the aperture and the second reservoir 18.

The molecular characterization enabled by the analysis device of the invention includes a wide range of analyses, including, e.g., sequencing, hybridization detection, molecular interaction detection and analysis, configuration detection, and other molecular characterizations. The molecules to be characterized can include, in general, any molecule, including polymers and biomolecules such as proteins, nucleic acids such as the polynucleotides DNA and RNA, sugar polymers, and other biomolecules. In one application, shown in the figure, the molecules to be characterized comprise single-stranded DNA molecules (ssDNA) 20 having a sequence of nucleoside bases 22 to be characterized, for example, by determining the identity of the sequence of bases along each ssDNA backbone. For clarity of discussion this sequencing example will be employed in the following description, but such is not the exclusive application of the molecular characterization device of the invention. In addition, the sequencing operation described below is not limited to the example of DNA; the polynucleotide RNA can similarly be characterized. The discussion below is therefore not intended to be limiting to a particular implementation, but provides details of one example in a range of embodiments for molecular characterization.

In operation of the molecular characterization device of FIG. 1A, application of a voltage bias between the two liquid compartments 16, 18, labeled "−" and "+" in the figure, causes molecules, e.g., ssDNA molecules, provided in the first compartment 16, to be electrophoretically driven, one at a time, into and through the nanopore 12 to the second compartment 18, because the DNA backbone is negatively charged when in solution. This voltage bias can be imposed by, e.g., the provision of silver chloride electrodes 17, 19 immersed in the solutions of the two compartments 16, 18, respectively, with corresponding voltage sources 21, 23, for controlling the voltage of each solution. An electrolytic solution of elevated pH or with selected denaturants is employed, as explained in detail below, to maintain the DNA strands in the first compartment 16 in an unstructured, single-stranded form prior to transport through the nanopore.

At the location of the nanopore 12 in the support structure 14 there are provided electrically-contacted probes 24, 26 for directly electronically characterizing the nucleosides in the translocating DNA molecules by local electron transport measurement. The probes 24, 26 serve as two nano-scale electrodes that abut the nanopore 12 at points on the perimeter of the nanopore, e.g., at opposite points of the nanopore perimeter. The probes 24, 26 are connected in an external electrical circuit 28 with a voltage source 30 for imposing a selected voltage bias between the probes, across the nanopore 12. Given that the electrolytic solution containing the molecules passes through the nanopore, between the probes, it is preferred that the support structure be provided as an electrically insulating structure and that an electrically insulating layer 15 or support structure region be provided to electrically insulate the probes except at the tips or very small local region of the probes that abut the perimeter of nanopore 12, as shown in FIG. 1A. This condition of electrical insulation enables the application of a selected voltage bias between the probes.

Given that the nanopore is a nano-scale gap, application of a voltage bias between the probes 24, 26 causes electron transport across the nanopore between the two probes, to complete the probe circuit 28. When a molecule such as a ssDNA nucleoside base 32 is positioned in the nanopore 12 between the probes 24, 26, the atomic structure of that base influences the electron transport across the nanopore. An ammeter 34 or other electrical current measurement device is provided in the circuit 28 for measuring the current associated with the nucleotide. In this manner, molecules translocating through the nanoscale aperture can be characterized; in this example, each of the nucleotides along the ssDNA molecule can be distinctly characterized, e.g., identified.

For a nano-scale aperture such as the nanopore 12, the dominant electron transport mechanism through an insulating DNA molecule, or other molecule, and the local electrolytic liquid environment in the nanopore is for many applications understood to be quantum mechanical electron tunneling. The term "tunneling" is here meant to refer to all types of electron transport across the nanopore, such as "hopping" from electronic state to electronic state, and other such transport, that is modulated by the presence of a molecule in the nanopore. Such electron transport is known to be very sensitive to local atomic structure and is therefore well-suited for distinctly characterizing molecules, e.g., for identifying nucleoside bases. But other electron transport mechanisms can occur alternatively or in addition to electron tunneling across the nanopore, and can be exploited for molecular characterization, such as a DNA sequencing operation. For example, mechanisms associated with induced charge effects, inelastic electron transport, or transport along a section of the length of a DNA molecule backbone can also be employed and are understood to provide sufficient sensitivity for discriminating between different nucleotide atomic structures as the nucleoside bases are transported through the nanopore.

Whatever electron transport mechanism takes place, the resulting current, which is sensed by the external circuit 28, is modulated by the individual nucleoside bases 22 as ssDNA molecules 20 translocate through the nanopore 12. This individual nucleotide characterization is enabled by the geometry of the nanopore, causing the nucleotides to pass in strictly sequential, single file order through the nanoscale aperture between the probes 24, 26. Measurement of the electron flow between the probes identifies the nucleotides, much as the electron flow between a scanning tunneling microscope tip and a surface can identify the atoms on the surface. Thus, the application of a voltage bias between the probes makes it possible to dynamically sense the transverse electrical conductivity of a translocating molecule.

This transverse electrical conductivity can be sensed in accordance with the invention through electron tunneling or other electron transport mechanism as described just above. The invention is not limited to a particular electron transport mechanism. In the discussion to follow, the electron transport mechanism of electron tunneling will be considered, but the invention is not limited to such. Typical electron currents in tunneling microscopes are nanoamps. This relatively large electron current, and the attendant relatively large signal to noise ratio, can be produced with the external circuit 28 in which the probes are connected.

Turning now to specifics of the probes 24, 26, at least one of the probes is provided as a fullerene structure such as a carbon nanotube. The term "fullerene structure" is herein meant to refer to any cage-like hollow molecular structure composed of ordered hexagonal and pentagonal groups of carbon atoms. One of the probes can also be provided as a metal conductor, but for many applications, it can be preferred to implement both probes 24 26 as fullerene structures such as carbon nanotubes. Carbon nanotubes are hollow tubes formed primarily of hexagonal groups of carbon atoms. Single-walled carbon nanotubes (SWNT) are one dimensional tubes that consist of a single rolled-up sheet of graphite having a crystalline, hexagonal, fullerene atomic structure. Carbon nanotubes can be synthesized with diameters as small as 7 Ångströms and lengths from sub-micron to millimeter. Carbon nanotubes are characterized by extreme mechanical and chemical robustness, and can be selected to exhibit either the excellent electrical transport properties of graphite or the band-gapped electronic structure of a semiconductor. Thus, the crystalline structure of carbon nanotubes provides a well-defined, predetermined, ordered, and robust morphology that can withstand the aqueous environment and high local electric field conditions of the nanopore; for many applications a metal conductor may not be expected to likewise do so.

In addition, because the electrical characteristics of carbon nanotubes are very sensitive to atomic scale perturbations, nanotubes are the preferred nanoscale probe for electronically differentiating between the four different DNA nucleoside bases translocating through a nanopore. Specifically, the van der Waals interaction of a DNA or RNA nucleoside coupled to a nanotube, as well as the electrical properties of a DNA or RNA nucleoside, can significantly affect the electronic properties of the nanotube by influencing the free charge carrier concentration and location of charge carrier energy levels, and corresponding conductivity, of the nanotube. Thus, the electronic properties of the nanotube-part of a coupled DNA base-nanotube hybrid play as important a role in determining the measurable contrast between analyzed DNA bases as do the molecules to be sequenced, the local environment near the molecule-nanotube hybrid, and the electrical conditions established by voltages applied to the nanotube probes and the ssDNA electrolyte solution.

In the example nanotube probe configuration of FIG. 1A, the nanopore provides a stable electron transport gap between cut ends of a single nanotube, or between the ends of two nanotubes, such that the nanotube ends can serve as electron source and sink for electron transport across the nanopore. With this arrangement, nano-scale resolution of the individual nucleoside base structures can be directly achieved and their electrical properties make it possible to detect and characterize many aspects of the polynucleotide, including its sequence. Example techniques for synthesizing nanotubes and fabricating nanotube probe arrangements are described in detail below.

The nanotube probes can be provided as metallic or semiconducting structures, but for many applications a small-gap semiconducting nanotube probe can be preferred to enable the production of measurable electron transport current at reasonable probe voltage biases. A single wall nanotube probe structure can also be preferred. The invention contemplates a range of fullerene structures to be employed as nanopore probes. For example, bucky ball fullerene spheres embedded in an electrically conducting medium can be employed as nanopore probes. Semiconducting nanowire structures can also be employed as nanopore probes. In the discussion to follow the example of nanotubes is employed but such is not intended to be limiting.

It has been discovered in accordance with the invention that the nanotube probes 24, 26, can be employed to physically orient nucleoside bases as the bases translocate through the nanopore, while at the same time producing a direct electronic signal that is indicative of the translocating bases, for characterizing the bases. This physical orientation is achieved in accordance with the invention by exploiting the affinity of DNA strands to closely couple with a surface of a carbon nanotube. When in the presence of a fullerene structure such as a carbon nanotube, each nucleoside base of a DNA molecule tends to form 11-stacking interactions with the nanotube fullerene structure, see for example Zheng et al., *Nature Materials* 2, 338-342, May 2003. A DNA molecule is understood to be quite flexible in bond torsion within the sugar-phosphate backbone, and it is this flexibility that accommodates the nucleoside base-nanotube coupling. In the coupling, the planar bases of a DNA molecule can individually be associated with, or coupled to, a nanotube surface by way of a non-covalent absorption process, in a condition whereby the plane of a base lays flat against the nanotube surface. As a result, in this configuration, a DNA nucleoside base is physically aligned by a nanotube surface to an orientation corresponding to that of the nanotube surface.

This phenomena of DNA-nanotube coupling is understood to be driven by free-energy considerations, electrical charge states, the complementary hydrophobic/hydrophilic nature of DNA bases and carbon nanotubes, and DNA backbones, respectively, and in part by the van der Waals interaction between a nucleoside base and the surface structure of a nanotube. No particular conditions need be imposed to enable the coupling of a nucleoside base to a nanotube surface. Indeed, it has been suggested that DNA or RNA will preferentially couple to nanotube surfaces rather than aggregate with itself.

Figure 1B:
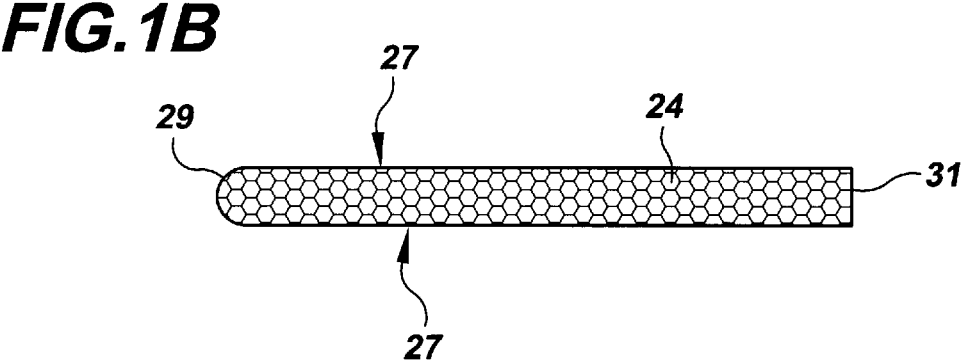
FIG. 1B is a schematic side view of a carbon nanotube, identifying the end and side of the nanotube.

In accordance with the invention, in the example configuration of FIG. 1A, a proximate nanotube probe is provided at a point along the length of the nanopore such that a DNA base will tend to align with a surface of the nanotube as the base is translocated through the nanopore. FIG. 1B is a schematic view of a nanotube 24, identifying the various nanotube surfaces available for coupling to a base and the terminology used herein for those surfaces. The nanotube 24 includes a side 27 to which a base can couple, and includes ends 29 and 31 to which a base can couple. The ends can be provided as a continuous extension of the graphitic surface, as in end 29, or can be a cut face end, as in end 31.

Figure 1C:
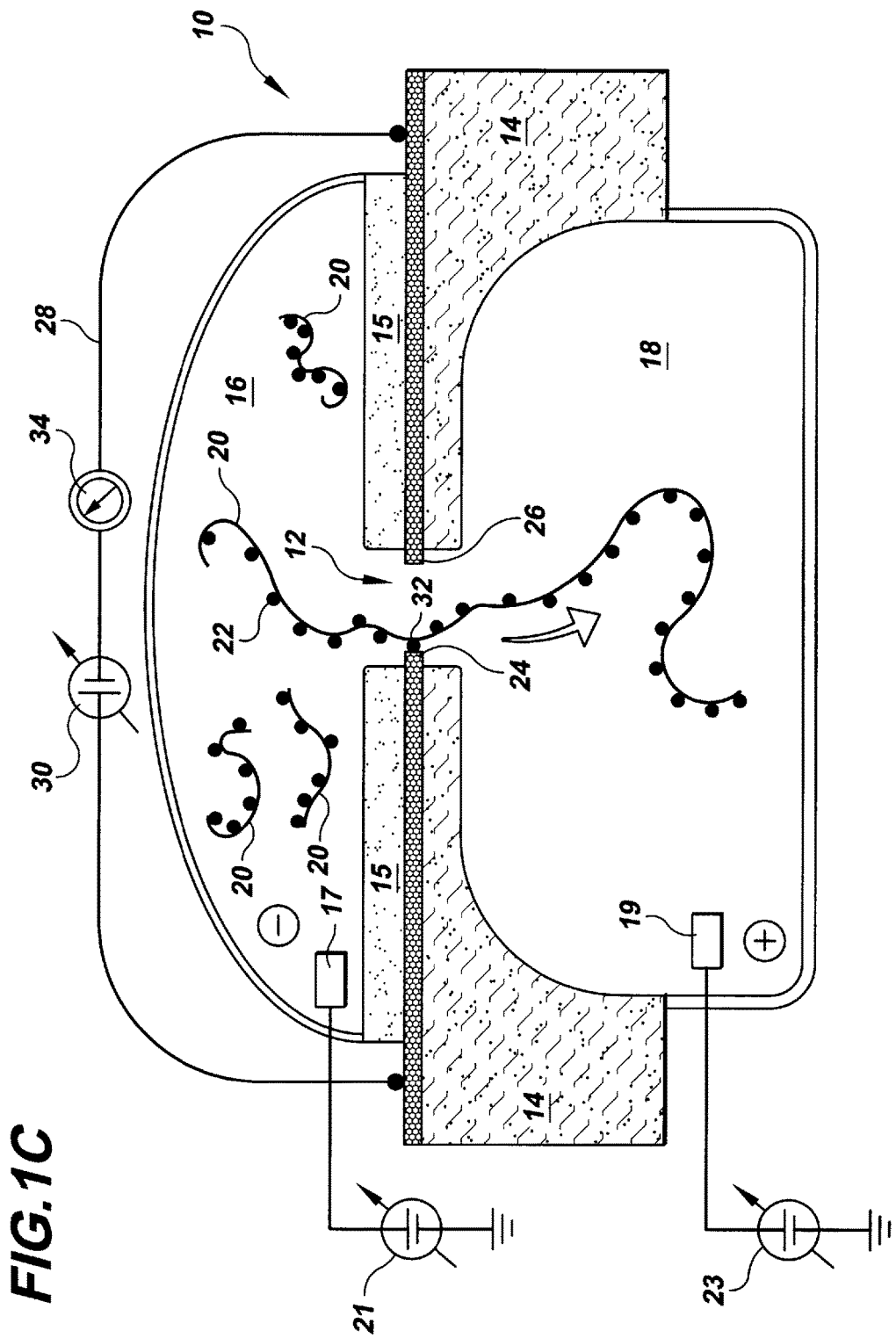
FIG. 1C is a schematic cross-sectional view of the device of FIG. 1A, shown here orienting a ssDNA molecule as the molecule is characterized.

FIG. 1C is a schematic view of the molecular characterization device of FIG. 1A, here shown at a time wherein a nanotube probe 24 is physically aligning a nucleoside base 32 as the base translocates through the nanopore. A nucleoside base 32 is coupled to an end of one 24 of the nanotube probes as the ssDNA 20 is translocated through the nanopore 12. As explained above, the planar nucleoside base 32 has a tendency to lay flat against the nanotube. This configuration enables a precise orientation of the base in the nanopore for detecting an electron transport current that is distinctly representative of the base. The coupling of the base with the nanotube end depicted in FIG. 1C is intended to be schematic only and does not represent particular details of the base orientation relative to the nanotube 24.

To enable the translocation and coupling depicted in FIG. 1C, the electrophoretic force across the nanopore is controlled to allow the nucleoside base 32 to slide along the nanotube end, with the electrophoretic force being sufficiently strong to cause the base to decouple from the nanotube end after some amount of time. This electrophoretic force control is implemented by control of the relative voltage between the two liquid compartments 16, 18 from control of the voltage sources 21, 23, respectively, in FIGS. 1A and 1C.

The binding energy between ssDNA and a nanotube has been estimated to be about −1.0 eV/nm, see, e.g., Zheng et al., "DNA-assisted dispersion and separation of carbon nanotubes," Nature Materials, 2, 338-342, 2003. The corresponding force needed to remove a nucleoside from an unbiased nanotube is therefore between about 3 pN and about 6 pN, which is approximately the electrophoretic force applied to a ssDNA traversing a nanopore having a voltage bias of between about 100 mV-200 mV across the nanopore, see, e.g., Sauer-Budge et al., "Unzipping kinetics of double-stranded DNA in a nanopore," Phys. Rev. Lett. 90, 2381011-2381014, 2003. Hence, the application of a 200 mV bias across the nanopore will, absent a bias on the nanotube probes, cause the nucleosides to slide across the nanotube end as shown in FIG. 1C. The coupling that occurs between a molecule and a carbon nanotube is therefore to be understood to be non-covalent, non-permanent, and of a nature that enables a molecule to slide along a nanotube surface while coupled to the surface.

As shown in FIG. 1C, the nanotube 24 to which the base 32 is coupled is positively biased with respect to the second nanotube 26. If the voltage of the nanotube 24 results in a positive bias of that nanotube relative to the electrolytic solution in the nanopore, then the negatively charged nucleotides will be prevented from sliding across the nanotube until the positive bias of the nanotube 26 is briefly reduced or until the bias across the nanopore, between the two liquid compartments, is raised sufficiently to slide the nucleotide across the nanotube. The invention therefore enables the control of translocation speed of nucleotides as well as orientation of the nucleotides as they translocate through the nanopore.

In the example configurations of FIGS. 1A and 1C the nanotube probes 24, 26 are shown to be oriented with an end of the nanotube abutting the perimeter of the nanopore. It is understood that the end of a nanotube can have a hexagonal carbon surface structure like that of the side of a nanotube, or other more complex detailed geometrical characteristic, and therefore can impose the same nucleotide orienting influence demonstrated by the side of a nanotube. If in a given application or configuration it is found that an end of a nanotube does not provide adequate orienting influence, then the nanotube end can be functionalized or otherwise processed, in the manner described below, to provide a terminating surface having the requisite nucleotide orienting characteristics.

With this example, it is shown that the nanotube probes enable both direct molecular characterization as well as molecular orientation control, and as described below, can further provide molecular translocation speed control. The nanotube probes are therefore not a simple alternative to conventional metallic probes and instead, based on the discovery of the invention, can be employed for enabling precise control of molecular characterization.

Figure 2A:
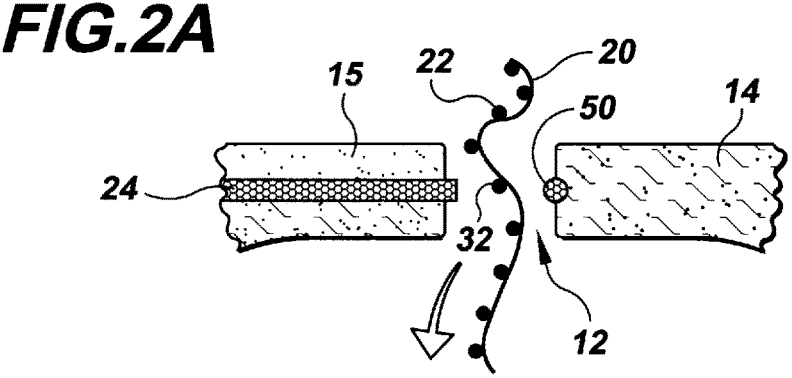
FIG. 2A is a schematic cross-sectional view of a further example embodiment of a molecular characterization device provided by the invention, articulated with one end-oriented nanotube probe and one side-oriented nanotube probe.

Referring to FIG. 2A, in a further embodiment provided by the invention, the molecular-orienting surface of one of the nanotube probes is provided as the side of a nanotube rather than a nanotube end. As shown in FIG. 2A, a first nanotube probe 24 is provided in the manner described above with an end disposed at a point along the length of a nanopore 12. The other nanotube probe 50 is disposed orthogonal to the first probe 24, so that a side of this probe 50 abuts the perimeter of the nanopore 12.

FIG. 2A is a cut-away sideview of the configuration, showing only the nanopore and the nanotube probes in a support structure 14, for clarity, but it is to be understood that liquid compartments, extended support structure, and electrical connections like that of FIG. 1A are included. In addition, as shown in FIG. 2A, the support structure and an electrically insulating region 15 are provided for electrically insulating the two nanotubes except where they abut on the nanopore perimeter.

Figure 2B:
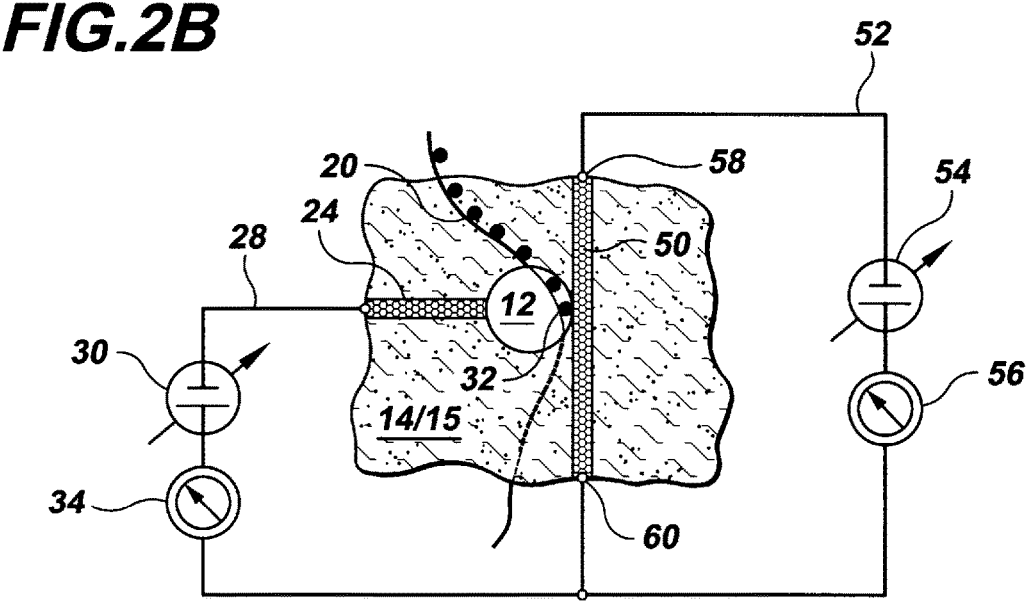
FIG. 2B is a schematic planar view of the embodiment of FIG. 2A.

The electrical connections for this configuration are shown in FIG. 2B, which is a schematic top-down, planar view of the assembly. Here is shown the nanopore 12 in a support structure 14, with an orthogonal positioning of the two nanotube probes 24, 50, resulting in a T-shaped probe arrangement. For clarity, the electrically insulating support structure and coating material that is located on top of the nanotube probes is not shown in FIG. 2B, enabling a direct view of the nanotube probe locations. With the arrangement of FIG. 2B, a first external circuit 28 is provided, in the manner described above with reference to the embodiment of FIGS. 1A-1B, to provide for application of a selected voltage bias 30 between the nanotube probes 24, 50. This electrical bias imposes a selected voltage across the aperture of the nanopore for stimulating electron transport across the nanopore as nucleoside bases of a DNA molecule are transported through the nanopore in the manner described above.

Figure 2C:
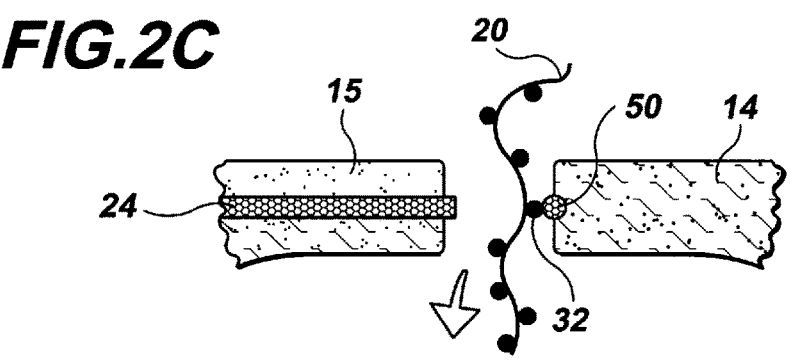
FIG. 2C is a schematic cross-sectional view of the embodiment of FIG. 2A, shown here orienting a ssDNA molecule as the molecule is characterized.

Referring also to FIG. 2C, there is shown the condition in which a nucleoside base 32 is coupled to the side of one 50 of the nanotube probes as the ssDNA 20 is translocated through the nanopore. This configuration enables a precise orientation of the base in the nanopore for detecting an electron transport current that is distinctly representative of the base. The base can slide along the side of the nanotube 50 as the base is characterized. Note also in FIG. 2C, with the polarity of the voltage source 30 as-shown in FIG. 2B, the side-oriented nanotube probe 50 is biased electrically positive relative to the end-oriented nanotube probe 24. If this positive bias is also positive with respect to the electrolytic solution, then as a result, as a nucleoside base 32 is drawn through the nanopore 12, the negatively-charged DNA backbone is electrically attracted to the side-oriented probe 50. The nucleoside base 32 interacts with, and couples to, the side of the probe 50 and remains coupled until the bias is reversed.

As a result, the side-oriented nanotube probe 50 can be further controlled for enabling control of nucleoside base translocation speed as a base is transported through the nanopore. Referring again to FIG. 2B, ends 58, 60 of the side-oriented nanotube probe 50 are connected in a second external circuit 52 provided with a voltage source 54 for separately controlling the voltage of the longitudinal nanotube probe 50; an ammeter or other current control and measurement device 56 can also be included in the second external circuit 52.

As explained above, the coupling of a DNA strand with a nanotube surface can at least in part be controlled by the relative electrical charge of the strand and the nanotube surface. Because a DNA backbone is inherently negatively charged when in solution, a positively charged nanotube surface, relative to the solution, tends to attract the DNA backbone to the nanotube surface. Conversely, a negatively charged nanotube surface tends to repel the DNA backbone from the nanotube surface. These conditions are exploited in accordance with the invention to control the duration of the coupling of a nucleoside base with the side-oriented nanotube probe.

Referring again to FIG. 2C, when the side-oriented nanotube probe 50 is electrically biased positively with respect to the electrolytic solution, the DNA backbone tends to be attracted to the side-oriented nanotube probe 50 and the nucleoside base 32 couples with the side-oriented nanotube probe 50. During this coupling, the electron transport that occurs between the nanotube probes, across the nanopore through the DNA base, can be measured for identifying the base.

Once this base identification measurement is complete, the second external circuit 52 is controlled to adjust the voltage source 54 and the corresponding electrical bias of the side-oriented nanotube probe 50. The voltage bias is now selected so that the side-oriented nanotube probe 50 is biased negatively with respect to the electrolytic solution, whereby the DNA backbone tends to be repelled from the side-oriented nanotube probe 50. With the initiation of the resulting repelling force, the nucleoside base 32 de-couples from the side-oriented nanotube probe 50, resulting in the configuration of FIG. 2A, and is transported further down through the nanopore by the electrophoretic force. The next sequential nucleoside base to be identified is correspondingly transported to the location of the nanotube probes for the next base identification cycle.

By enabling this base identification cycling, the embodiment of FIGS. 2A-2C imposes on a DNA strand both translocation speed control as well as physical orientation control on nucleotides of the strand as those nucleotides translocate through a nanopore. The example implementation of FIGS. 2A-2C is particularly advantageous in that the side-oriented nanotube probe 50 provides nanotube ends 58, 60 away from the nanopore and at which electrical connection to an external circuit 52 can be made. But if necessary or desirable for a given implementation, the end-oriented nanotube probe 24 can instead be separately controlled with the second external circuit 52 for causing controlled coupling and de-coupling of a DNA nucleotide to the end-oriented nanotube probe 24 rather than the side-oriented nanotube probe 50.

As explained above, it is understood that a DNA nucleotide has a tendency to couple with both the ends of a nanotube as well as the sides of a nanotube. Whether a nanotube end or a side is employed for DNA coupling, the invention does not require that all nucleoside bases be oriented identically by a nanotube surface. Instead, it is preferred that all nucleoside bases of a common type be oriented substantially similarly; i.e., all T bases should be oriented similarly, all G bases should be oriented similarly, and so on. With this condition met, it can be assured that each instance of a given base type will result in an expected orientation or in a limited class of orientations, and therefore will aid in contrasting between the four DNA bases and facilitate precision of sequencing.

Further, the invention does not require a particular orientation for coupling of a nucleoside base to a nanotube surface. It is understood that under many conditions, the plane of a nucleoside base tends to lay flat against a nanotube surface, as explained above. But such is not universally required by the invention. A nucleoside base can be arranged at some angle with a nanotube surface, can effectively stick off the surface, or be oriented in any suitable manner that enables electronic detection of its identity. As explained above, it is preferred that each instance of a given base type be oriented similarly, to enhance base contrast precision, but no particular orientation is required.

Figure 3A:
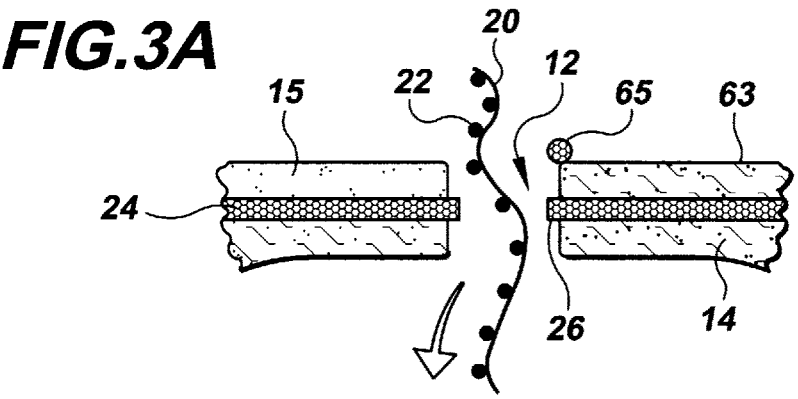
FIG. 3A is schematic cross-sectional view of a further example embodiment of a molecular characterization device provided by the invention, articulated with end-oriented carbon nanotube probes and a side-oriented translocation control carbon nanotube.

In a further embodiment provided by the invention, molecular translocation control can be implemented separately from the electron transport nanotube probe configuration. FIG. 3A is a schematic cross-sectional view, not to scale, of an example of such an arrangement. As in FIGS. 2A and C above, it is to be understood that the liquid compartments and associated voltage sources are included as in FIG. 1A, and that electrical insulation of both nanotube probes is provided, with only the ends of the nanotubes abutting the nanopore being un-insulated.

In FIG. 3A there are shown two nanotube probes 24, 26 in a support structure 14, in the manner of FIG. 1A, across a nanopore 12. The nanotube probes are in this example arranged with an end-orientation at the nanopore perimeter. At the support structure surface 63 at which a DNA strand 20 is to enter the nanopore 12 there is provided a side-positioned nanotube 65 at the perimeter of the nanopore 12. The electrical bias of this surface-positioned nanotube 65 is controlled in the manner of the side-oriented nanotube probe 50, in FIGS. 2A-2C, for controlling the translocation speed of the DNA strand being transported through the nanopore 12 for base identification at the location of the nanotube probes 24, 26.

Figure 3B:
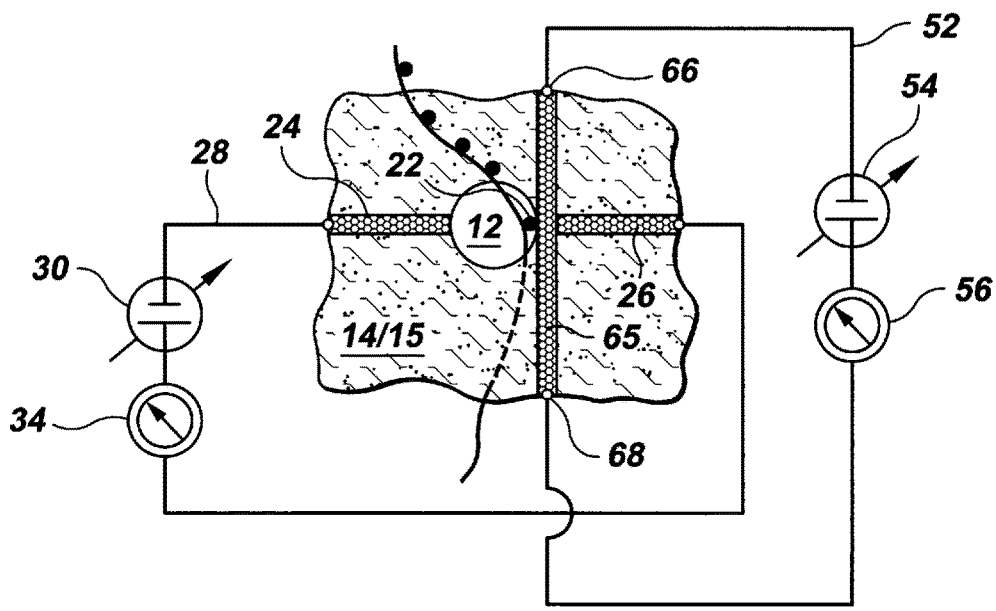
FIG. 3B is a schematic planar view of the embodiment of FIG. 3A.

FIG. 3B is a top down planar view of the configuration of FIG. 3A, here including the external circuit connections for the configuration. In this view, the nanotube probes 24, 26 are indicated with dotted cross-hatching as underlying the surface of the support structure 14 at a point along the length of the nanopore 12. The surface-positioned nanotube 65 is purely cross-hatched to indicate its position above the nanotube probes 24, 26, on the surface of the support structure 14. A first external circuit 28 like that of FIG. 1A is provided for the two nanotube probes 24, 26. A voltage source 30 in the circuit 28 enables application of a selected voltage bias between the nanotube probes 24, 26 for causing electron transport across the nanopore and enabling electrical current measurement for nucleoside base identification, in the manner previously explained.

A second external circuit 52, like that of FIG. 2B, is provided for electrically biasing the surface-positioned nanotube 65. The ends 66, 68 of the surface-positioned nanotube 65 are connected in the second external circuit 52 provided with a voltage source 54 for controlling the voltage of the surface-positioned nanotube 65; an ammeter or other current control and measurement device 56 can also be included in the second external circuit 52.

Figure 3C:
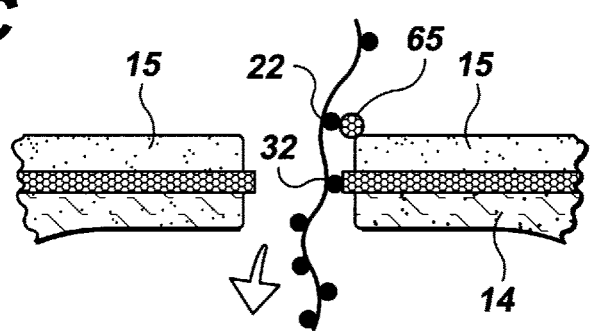
FIG. 3C is a schematic cross-sectional view of the embodiment of FIG. 3A, shown here controlling translocation speed and orienting a ssDNA molecule as the molecule is characterized.

Referring also to FIG. 3C, when the surface-positioned nanotube 65 is electrically biased positively with respect to the electrolytic solution, the DNA backbone tends to be attracted to the surface-positioned nanotube 65 and a nucleoside base 32 couples with the surface-positioned nanotube 65. This acts to control the forward translocation speed of the DNA strand through the nanopore. The coupling of the base 32 to the surface-positioned nanotube 65 also spatially orients the base by orienting the base on the nanotube surface. At the same time, the first external circuit 28 imposes a voltage bias between the nanotube probes 24, 26. The resulting electron transport that occurs between the nanotube probes, 24, 26, across the nanopore through the DNA base located at the position of the nanotube probes 24, 26, can at this time be measured for identifying the base at the position of the nanotube probes 24, 26.

Once this base identification measurement is complete, the second external circuit 52 is controlled to adjust the voltage source 54 and the corresponding electrical bias of the surface-positioned nanotube 65. The voltage bias is now selected so that the surface-positioned nanotube 65 is biased negatively with respect to the electrolytic solution, whereby the DNA backbone tends to be repelled from the surface-positioned nanotube 65. With the initiation of the resulting repelling force, the nucleoside base 32 de-couples from the surface-positioned nanotube 65, resulting in the configuration of FIG. 3A, and is transported into the nanopore by the electrophoretic force. The next sequential nucleoside base to be identified is correspondingly transported to the location of the nanotube probes for the next base identification cycle. The nucleoside base orientation that was carried out at the surface-positioned nanotube 65 may remain with the base as it enters the nanopore and approaches the nanotube probes, depending on the length of the nanopore. This orientation control is then reinforced by the coupling of the base to one of the nanotube probes as the base arrives at the location of the probes along the nanopore length.

In an alternative implementation, the surface-positioned nanotube 65 can be end-oriented at the perimeter of the nanopore 12 rather than side-oriented at the nanopore perimeter. This end-orientation of the surface-positioned nanotube disposes an end at the nanopore edge in the manner of the end-oriented nanotube probes 24, 26 described above. This implementation may be less preferable, however, in that such does not provide two nanotube ends at locations away from the nanopore perimeter for making contact to the nanotube. If, however, a given application accommodates contact to the end face-oriented surface of a surface-positioned nanotube, then such can be employed where applicable.

In a further embodiment of the invention, the first external circuit 28 shown in the example implementations of FIGS. 1, and 3 can be controlled in the manner of the second external circuit 52 shown in FIGS. 2B and 3B to transiently bias the end-oriented nanotube tunneling probes 24, 26 (FIGS. 1 and 3). Transient nanotube probe biasing is here imposed to enable with only a single circuit the translocation control achieved by the second external circuit 52 as in the example implementation of FIG. 2B. It is understood in accordance with the invention, and as explained above, that the electrical charge of the two nanotube probes causes the negatively charged DNA backbone to be attracted to that nanotube probe which is biased most positively with respect to the electrolytic solution. When a voltage bias is applied between the nanotube probes, the DNA backbone is attracted to the positively charged nanotube probe, and the nucleoside base at that position couples with the positively charged nanotube probe. This coupling acts to slow or halt the progression of the strand through the nanopore. When the voltage bias is reversed with respect to the electrolytic solution, the DNA backbone is repelled from the nanotube to which the base was coupled, and the DNA strand can then proceed through the nanopore. Control of the DNA strand translocation is thusly achieved.

Use of this transient nanotube probe scenario with the implementation of FIG. 1 enables the two nanotube probes 24, 26 to conduct both spatial molecular orientation control as well as molecular translocation speed control. In the implementation of FIG. 3 this transient nanotube probe bias control enables dual translocation speed controls imposed by the surface-positioned nanotube 66 and the nanotube probes 24, 26. The two translocation controls here can be operated synchronously to cause a ratchet-like translocation of the DNA strand through the nanopore.

Figure 4B:
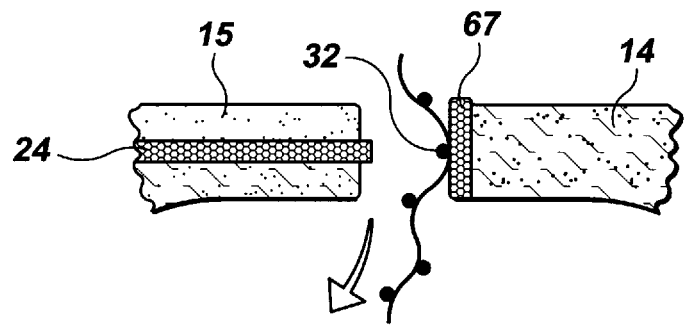
FIG. 4B is schematic cross-sectional view of a further example embodiment of a molecular characterization device provided by the invention, articulated with one end-oriented carbon nanotube probe and one side-oriented nanotube probe extending through the length of a nanopore.

In accordance with the invention, the various features and control techniques incorporated into the example configurations of FIGS. 1-3 can be selected as-desired for a given molecular characterization application in a wide range of alternative arrangements. For example, as shown in the cross-sectional cut-away view of FIG. 4A, nanotube tunneling probes can be provided as an end-oriented probe 24 and a side-oriented nanotube probe 50. A surface-positioned nanotube 65 can further be provided for imposing additional molecular translocation speed control. All of the nanotubes are electrically insulated, except for the end or side of the nanotube abutting the nanopore. As shown in FIG. 4B, nanotube probes can further be provided as, e.g., an end-oriented probe 24 and a side-oriented nanotube probe 67 that extends horizontally through the thickness of the support structure, along the inside length of the nanopore. With this arrangement, a nucleoside base can slide along the side-oriented nanotube 67 through the full nanopore length in a well-controlled orientation. To enable this condition, the side-oriented probe here is not insulated along the region of the probe exposed in the nanopore, as explained in the examples below. As can be recognized, the end-oriented probe 24 can also be provided as a side-oriented probe like the side-oriented probe 50 shown in FIG. 4A.

Each of these device arrangements can be controlled by one or more selected external biasing circuits for imposing time-dependent orientation and translocation speed control. For example, a first bias circuit like the external circuit 28 in FIG. 1A can be employed between the nanotube probes 24, 50, and a second bias circuit like the external circuit of FIG. 2B can be employed to separately control the bias of the longitudinal nanotube probe 50. A further control circuit like the external circuit 52 in FIG. 3B can further be employed for controlling the bias of the surface-oriented nanotube 65.

The example device configurations discussed above have been described as operating by measuring electron transport through a molecule in a nanopore, between nanotube probes. The invention does not limit the device configurations to such operation, however. It is also recognized that the proximity of a molecule to a nanotube can change the conductance of the nanotube along the nanotube length, by inducing changes in the concentration of nanotube electronic carriers available for electronic transport along the length of the nanotube, as described above, and/or by modulation of the electrical mobility of such electronic carriers. Therefore, all of the device configurations that accommodate interaction of a molecule with a side of a carbon nanotube can also be operated in what can be termed an "FET mode." Examples of such configurations are those shown in FIGS. 2A-C (nanotube probe 50), FIGS. 3A-3C (nanotube 65), and FIG. 4A (nanotubes 50 and 65).

In the FET mode of operation, an electrical bias voltage is applied across opposite ends of a nanotube having a side that forms the molecular contacting and orienting surface, e.g., nanotubes 50 and 65 in FIGS. 2-4. This bias can be applied with the circuit 52 in FIGS. 2B and 3B, connected to nanotubes 50 and 65. The conductance of these nanotubes is sensitive to the proximity and characteristics of a molecule in the nanopore. Thus, measurement, in the circuit 52, of the electrical current through the nanotube 50 or 65 as a molecule translocates through the nanopore provides an alternative technique for electronically characterizing a molecule with a side-oriented nanotube-based characterization device. The invention thus is not limited to a particular mode of operation of the molecular characterization devices of the invention.

In addition, in all of the implementations of FIGS. 1-4, the voltage bias of each of the solutions in the two liquid compartments can be adjusted in a time-dependent manner to control the electrophoretic force driving a molecule through the nanopore relative to the molecule-nanotube coupling force, as explained above. For example, the electrodes 17, 19 in the first liquid compartment 16 and second liquid compartment 18, respectively (FIG. 1A), can be selectively biased over time, e.g., in synchrony with applied nanotube probe bias control and translocation speed bias control. Such liquid bias provides a further level of control over the bias of the nanotube probes relative to the electrolytic solution, and thus enhances the precision of molecular translocation control. Such precision can be desirable to achieve a translocation speed that is commensurate with the sensitivity and bandwidth of the measurement electronics. At a translocation speed of, e.g., about $10^4$ bases/sec, measurements of distinct electron transport signals for sequential bases can be resolved. Thus, with electrical bias control applied to a selected arrangement of nanotubes and external circuits, there can be achieved control of the rate of DNA translocation and the physical orientation of the DNA nucleoside bases in a manner that accommodates direct electronic discrimination between the different nucleoside bases.

As a result of these capabilities, the molecular analysis device of the invention functions as a very high throughput sequencing device, even though the nanopore operates as a single molecule detector. Thousands of different molecules or thousands of identical molecules can be probed in a few minutes with the molecular analysis device of the invention. Because the method of operation of the nanopore device directly converts characteristic features of a translocating molecule into an electrical signal, transduction and recognition can occur in real time, on a molecule-by-molecule basis. Further, long lengths of DNA can be probed in this real time fashion. While practical considerations of sample preparation or of a particular application may limit the length of a DNA strand that can be analyzed as the strand translocates through a nanopore, there are no theoretical limits to analyzed strand length.

Figure 5A:
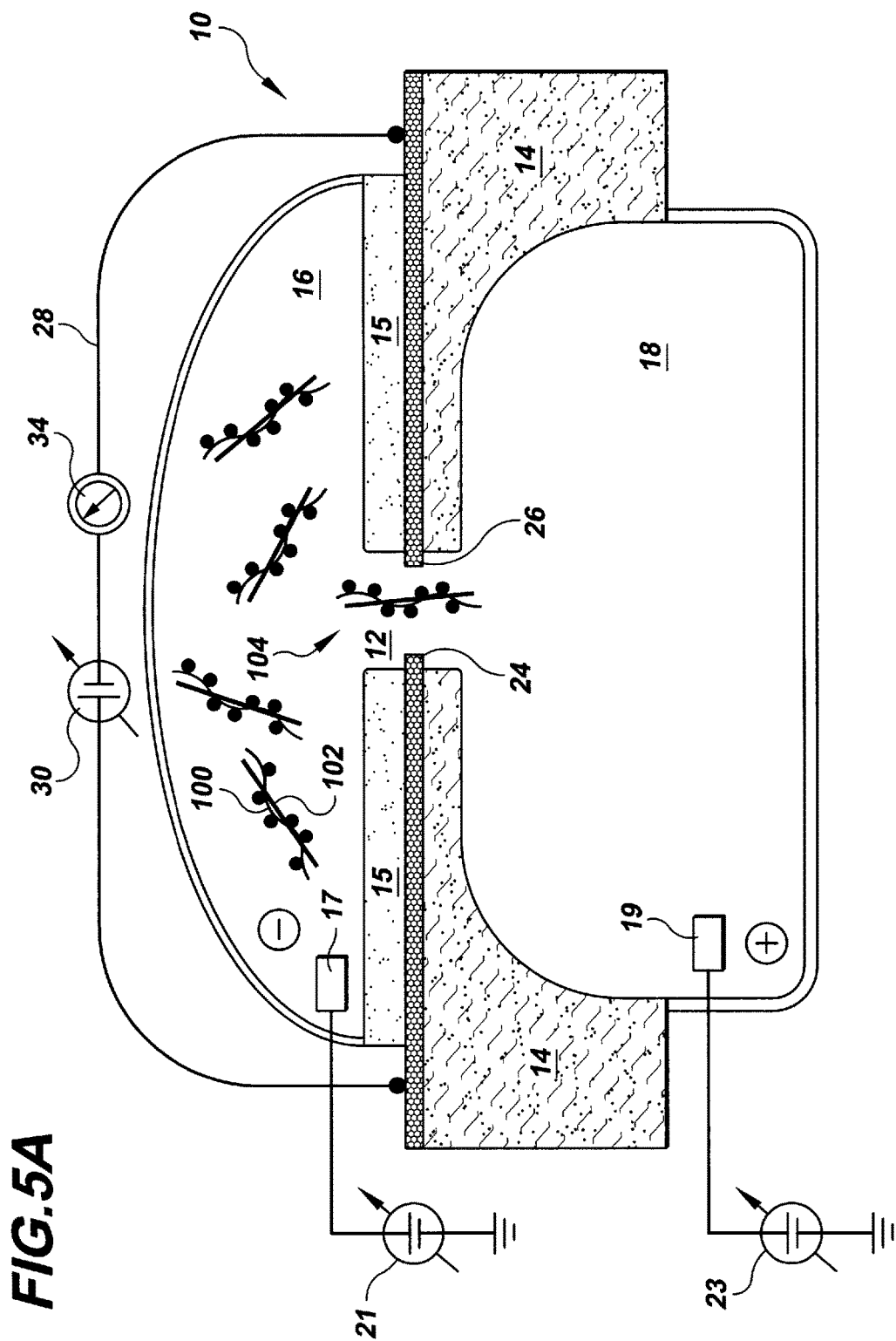
FIG. 5A is a schematic cross-sectional view of a further example embodiment of a molecular characterization device provided by the invention, articulated with end-oriented carbon nanotube probes, and configured for translocation and characterization of DNA-nanotube complexes through a nanopore.

Turning now to further embodiments of the molecular analysis device of the invention, and referring to FIG. 5A, in a further molecular analysis technique of the invention, DNA sequencing is conducted by translocation, through a nanotube-articulated nanopore, of complexes of DNA strands coupled to free nanotubes. In a device provided by the invention for conducting this process, as shown in FIG. 5A, in a first liquid compartment 16 there are provided, in solution, ssDNA molecules 100 which have been coupled to nanotubes 102, with at least one DNA strand 100 coupled to separate nanotubes 102. Such a solution of DNA-nanotube complexes can be formed and processed by, e.g., gel electrophoresis, to provide desired molecule-nanotube complexes as taught in U.S. Patent Application Publication No. 2005/0009039, Jagota et al., "Dispersion of Carbon Nanotubes by Nucleic Acids," the entirety of which is hereby incorporated by reference.

The first liquid compartment is in communication with a nanopore 12 provided in a support structure 14 in the manner described above. At a point along the length of the nanopore are disposed nanotube probes 24, 26. The nanotube probes can be provided as end-oriented probes, in the manner shown in FIG. 5A, or can be side-oriented, e.g., in the manner shown in FIG. 2A.

Application of a voltage bias between the two liquid compartments 16, 18, labeled "−" and "+" in the figure, causes the DNA-nanotube complexes in the first compartment 16 to be electrophoretically driven, one at a time, into and through the nanopore 12 to the second compartment 18. This voltage bias can be imposed by, e.g., the provision of silver chloride electrodes 17, 19 immersed in the solutions of the two compartments 16, 18, respectively, with corresponding voltage sources 21, 23, for controlling the voltage of each solution.

A voltage bias is applied between the nanotube probes 24, 26, across the nanopore, by an external circuit 28 having a controllable voltage source 30. When a DNA-nanotube complex 104 is translocated into the nanopore and translocates between the nanotube probes 24, 26, electron transport between the nanotube probes 24, 26 is influenced by the presence of the DNA-nanotube complex 104. An ammeter 34 or other current measuring element is provided in the external circuit to monitor the resulting current for identifying the bases of the DNA-nanotube complex. Given that each nucleoside base of a DNA molecule is coupled to the longitudinal sidewall of a nanotube in a DNA-nanotube complex, then as the DNA-nanotube complex translocates through the nanopore 12, each nucleoside base of the coupled DNA strand is separately and distinctly identified by changes in the electron transport between the nanotube probes. It is to be recognized that the coupling of the DNA molecule to the carbon nanotube can result in a reduction in speed of molecular transport through the nanopore, relative to an un-coupled DNA strand, due to the added viscous drag of fluid near the nanopore caused by the presence of nanotubes. But fluctuations in DNA strand movement due to Brownian motion are reduced by the coupling of the DNA strand to a nanotube, due to the large mass and rigidity of the nanotube.

In addition to this electronic analysis of a translocating DNA-nanotube complex, changes in the ionic current flowing in solution through the nanopore from the first liquid compartment 16 to the second liquid compartment 18, in the manner described previously, can be monitored to ascertain the location of a translocating DNA-nanotube complex. Given that the dimensions of the nanopore correspond to that of the DNA-nanotube complex so that a complex occupies a large fraction of the nanopore's cross-sectional area during translocation, the complex transiently reduces, or blocks, the ionic current resulting from the voltages applied to the first and second liquid compartments in the manner described above. As a result, measurements of the ionic current between the first and second liquid compartments can be employed to indicate if a DNA-nanotube complex is within the nanopore. Such an indication can be synchronized with control of the external circuit for initiating measurement of electron transport current once presence of a DNA-nanotube complex in the nanopore is confirmed.

The slowing and orientation effects of the DNA carbon nanotube hybrid complex can be used to advantage for molecular characterization with either ionic current flow or electron current flow molecular characterization devices. The invention contemplates the characterization of a DNA-nanotube complex by either electron current flow, as in the nanotube probe configurations described above, or in an ionic current flow measurement technique. The measurement of the ionic current between the first and second liquid compartments can be employed to indicate a range of features of a DNA molecule that is complexed with a nanotube. For example, complementary base-paired sequences of monomers that cause "hairpin" loops to be formed within a polynucleotide strand are distinctly oriented on the nanotube, and hence produce modulations of the ionic current that are different than that of non-complementary sequences. Thus, the DNA-nanotube complex can be characterized in a suitable manner, e.g., with ionic current flow monitoring, without inclusion of detection of electron current flow modulation.

In the example embodiment of FIG. 5A, each free nanotube 102 provides physical orientation of the nucleotides of the DNA strand 100 coupled to that nanotube. When a DNA-nanotube complex 104 translocates through the nanopore 12, additional orientation control can be imposed by the nanotube probes 24, 26 in the manner described above. For example, the voltage bias between the nanotube probes 24, 26 can be controlled to attract the negatively-charged DNA backbone, and the nanotube to which it is coupled, to the positively charged nanotube probe 24. This enables spatial orientation control of the DNA-nanotube complex within the nanopore between the nanotube probes.

If desired for a given application, the various nanotube configurations in the examples of FIGS. 1-4 can be implemented to control the orientation as well as translocation speed of a DNA-nanotube complex as the complex is translocated through the nanopore. In addition, as explained above, the electrophoretic force between the two liquid compartments can be controlled by adjusting the voltage bias of the two liquid compartments to further control the DNA-nanotube complex translocation speed.

Figure 5B:
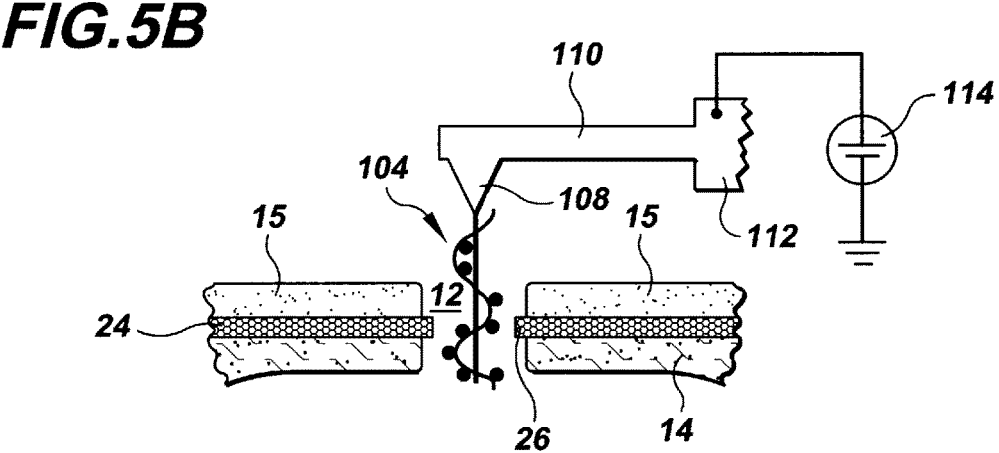
FIG. 5B is a schematic cross-sectional view of a further example embodiment of a molecular characterization device provided by the invention, articulated with end-oriented carbon nanotube probes, and configured for translocation of actuator tip-mounted DNA-nanotube complexes through a nanopore.

Turning to FIG. 5B, in a further embodiment of the invention, the translocation of a DNA-nanotube complex through a nanopore can be strictly controlled by an externally-commanded actuating element. In this arrangement provided by the invention, a DNA-nanotube complex 104 to be analyzed is provided mounted on a tip 108 of a cantilever 110 or other moveable element that can be actuated by a controlling mechanism 112. In one example embodiment, the mounting tip 108 is located at the end of a cantilever 110 of an atomic force microscope (AFM). Any suitable actuated and moveable tip structure can be employed as the mounting tip. Scanning tunneling microscope tips, microelectromechanical (MEMs) structures such as actuated micromachined cantilever beams and bridges, and other system apparatus or custom-fabricated mechanical arrangements can be employed for the DNA-nanotube complex mounting tip.

Whatever tip configuration is employed, the tip-mounted DNA-nanotube complex is translocated through a nanopore 12 in a support structure 14, moving between two nanotube probes 24, 26. With precise control of the tip 108 and cantilever 110, the tip-mounted DNA-nanotube complex can be slowly advanced, e.g., at a translocation speed as low as approximately 1 nucleoside base/second, through the nanopore 12. At the location of the nanotube probes 24, 26, electron transport across the nanopore, through the DNA-nanotube complex, is influenced by the presence of the DNA-nanotube complex. In the manner described above, an external circuit can be employed to measure the electron transport for discriminating between the nucleoside bases of the DNA molecule in the DNA-nanotube complex. For applications in which external circuit measurement bandwidth may be limited, this arrangement can be advantageous for precisely controlling translocation speed in a manner that accommodates the circuit bandwidth.

It is to be understood that the external bias and measurement circuit 28 of FIG. 5A, while not shown in FIG. 5B for clarity of discussion is to be included in the configuration of 5B for enabling nanotube probe bias and electron transport measurement. Further, for many applications, the liquid compartments 16, 18 of FIG. 5A are preferably further included in this configuration to provide a medium in which the DNA-nanotube molecules can easily translocate through the nanopore, and to enable additional bias control.

In a further control technique, an additional voltage source 114 can also be provided for electrically biasing the DNA-nanotube complex 104 translocating through the nanopore. Like biasing the gate or base of a conventional transistor, bias of the DNA-nanotube complex influences electron transport between the nanotube probes. The voltage applied to the DNA-nanotube complex changes the spatial intimacy of the DNA coupling to the nanotube and correspondingly adjusts the energy levels of the DNA-nanotube complex that are available to electrons transported between the nanotube probes. The voltage applied to the DNA-nanotube complex can therefore be controllably varied to adjust and enhance the resolution and contrast of electron transport measurements for nucleoside base identification.

The electrostatic potential of the liquid solution in which the DNA-nanotube complex is translocated can also be adjusted, in the manner described above, for further tuning of the electron transport.

With a voltage applied to the DNA-nanotube complex, the nanotube of the complex can itself be employed as an electron transport probe in the manner of the nanotube probes 24, 26. In this scenario, one of the nanotube probes 24, 26 can be eliminated so that the electron transport for nucleotide analysis occurs between one nanotube probe, e.g., probe 24, and the nanotube of the DNA-nanotube complex 104. The external circuit for measuring current flow, like the circuit 28 of FIG. 5A, is in this case connected between the one nanotube probe 24 and the cantilever actuator 112.

Figure 5C:
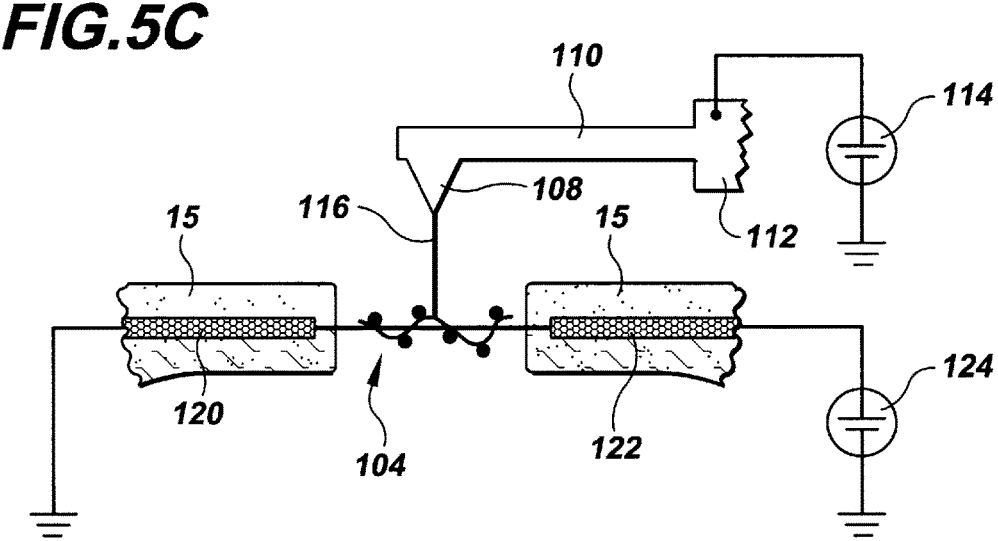
FIG. 5C is a schematic cross-sectional view of a further example embodiment of a molecular characterization device provided by the invention, configured with an actuator tip-mounted carbon nanotube probe for scanning a DNA-nanotube complex.

The invention provides an experimental configuration for verifying the nature and characteristics of DNA-nanotube complexes to be analyzed by the devices of FIGS. 5A-5B. One example implementation of this experimental configuration is shown in FIG. 5C. As shown in FIG. 5C, there is provided a DNA-nanotube complex 104 suspended between two electrically contacted electrodes 120, 122. The electrodes 120, 122 can be provided as any suitable conductor, e.g., as metallic electrodes or as nanotubes. The electrodes 120, 122 are connected in a circuit with a voltage source 124 for electrically biasing the suspended DNA-nanotube complex 104.

An electrically-contacted probing nanotube 116 is provided mounted on the tip 108 of a cantilever 110, e.g., provided by an AFM 112. A voltage source 114 is provided for electrically biasing the tip-mounted probing nanotube 116. With this configuration, the AFM is first operated in the traditional AFM mode to enable the tip-mounted probing nanotube 116 to locate the suspended DNA-nanotube complex 104. Then the AFM is operated in scanning tunneling microscopy mode (STM) to record electronic images of the DNA-nanotube complex as the probing nanotube 116 is scanned along the suspended complex 104. The resulting images geometrically reveal each base along the backbone of the coupled DNA strand.

If necessary, scanning of the suspended DNA-nanotube complex can be conducted with the complex in a dry state. In this case, it is preferred that the complex be dried from, e.g., a solution including volatile salts such as ammonium acetate and an amount of methanol sufficient to reduce the surface tension below that which would disrupt the complex structure during the drying process. For many applications it can be preferred to conduct the scanning in a liquid environment that simulates the liquid solutions employed in the sequencing configurations of FIGS. 5A-5B.

Whatever the scan environment, as the scan proceeds, the tunneling bias voltage of the probing nanotube 116 can be adjusted upon arrival at each nucleoside base along the DNA strand to explore the electron transport characteristics of that base. This information is then employed in accordance with the invention to optimize the bias to be applied to the nanotube probes in the configurations of FIGS. 5A-5B for enhancing contrast between the four different DNA bases.

The example molecular characterization devices described above are in general configured in a solid state support structure, e.g., a structure formed of a microelectronic material, for example, employing the materials and arrangements taught in U.S. Pat. No. 6,627,067, Branton et al., "Molecular and Atomic Scale Evaluation of Biopolymers," the entirety of which is hereby incorporated by reference.

Figure 6:
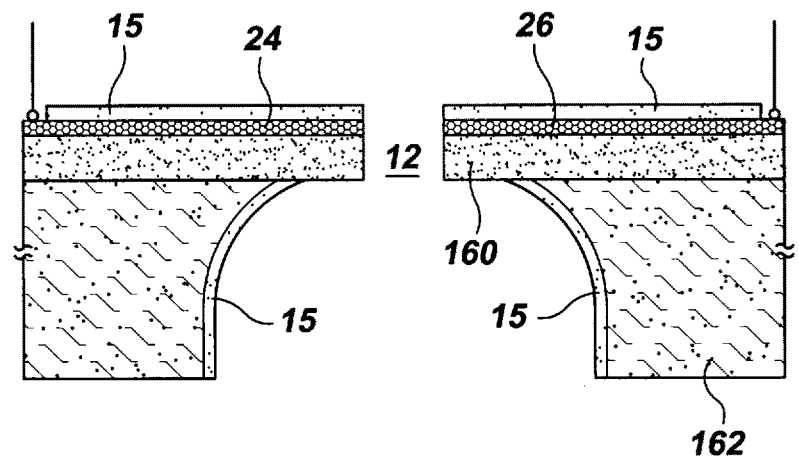
FIG. 6 is a schematic cross-sectional view of a molecular characterization device provided by the invention, configured with a nanopore in a silicon nitride membrane on a silicon support frame.

Turning to particular aspects of the molecular characterization device fabrication features, the solid state support structure in which a nanopore is provided is in general formed of a microelectronic material, e.g., a silicon-based material such as single crystal silicon, silicon nitride, or polysilicon. In one particularly well-suited configuration, the support structure in which a nanopore is provided is formed of a membrane on a support structure, e.g., a silicon nitride membrane on a silicon support frame. This configuration is shown in FIG. 6. Here is provided a suspended silicon nitride membrane 160 on a silicon support frame 162, fabricated in the conventional manner. Silicon nitride is a particularly well-suited material because of its generally electrically insulating property and resistance to degradation by a wide range of liquids. A range of other materials can be employed for the membrane in which a nanopore is provided, however; the membrane material is in general preferably chemically inert and/or resistant. Exemplary materials include silica, alumina, plastics, polymers, elastomers, glasses, or other suitable material.

Carbon nanotubes 24, 26 are provided on the membrane 160, in the manner described below, with a nanopore at the center of the membrane. All surfaces of the device in contact with the electrolytic molecule-bearing solution are electrically insulated, except for the surfaces of the nanotubes that abut the nanopore perimeter. The silicon nitride membrane, being electrically insulating, inherently provides for insulating nanopore walls. The nanotubes 24, 26 and silicon support frame 162 are preferably coated with a layer of electrically insulating material 15, e.g., alumina, hafnium oxide, or other selected insulating material.

The discussion below provides details of formation of an aperture that can be sized as a nanopore in a membrane and support structure. In general, the nanopore is sized for interaction with a molecule of interest; that is, the nanopore is of a diameter that is similar to the atomic width of a molecule of interest. For applications in which, e.g., a single-stranded polynucleotide is to be translocated through the nanopore, a nanopore diameter in the range of about 1 nm-20 nm can be preferred. No specific constraints are placed on the nanopore geometry other than that it be adequate to permit only a single polymer molecule at a time to traverse the nanopore, and that the molecule travel in an extended conformation, e.g., without secondary structure. A generally circular nanopore geometry can be preferred but is not required; non-circular nanopore profiles can also be employed.

Further, there is no particular length requirement of the nanopore; a nanopore length of, e.g., about 0.1 nm-800 nm can be employed and produced by processing of, e.g., a silicon nitride membrane. As explained above, in order to accommodate electron transport across the nanopore, the walls of the nanopore are electrically insulating. If the membrane is itself an insulating material, then no additional nanopore wall processing is required, aside from the considerations discussed below. If the membrane is electrically conducting, the walls of the nanopore can be coated with a selected insulating layer in the manner described below.

Figure 7:
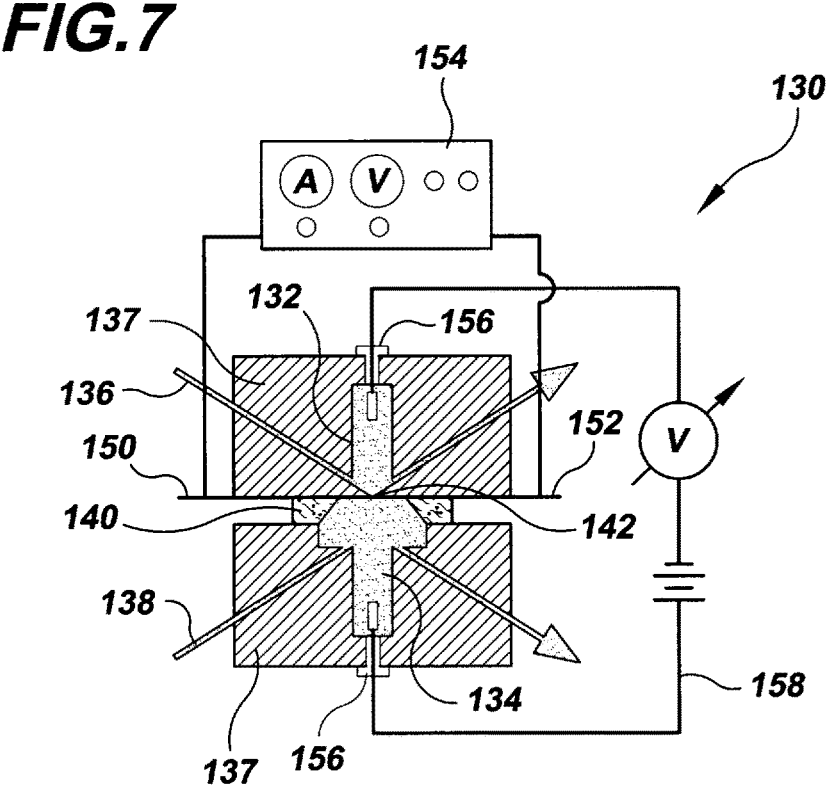
FIG. 7 is a schematic view of a packaged molecular characterization device provided by the invention including fluid reservoirs and channels.

FIG. 7 is a schematic view of an example housing configuration 130 for packaging a microfabricated molecular characterization device system like that of FIG. 6, and for connecting such to the requisite circuitry. As shown in FIG. 7, the example housing configuration includes liquid reservoirs 132, 134, along with liquid channels 136, 138, in, e.g., a silicone rubber (PDMS) chip holder 137, to implement liquid compartments for the molecule-bearing electrolytic fluid to be translocated through a nanopore. A microfabricated structure, e.g., a silicon frame 140, is provided for supporting, e.g., a membrane in which a nanopore 142 is provided. Nanotube probe contact pad connections 150, 152 are provided for making electrical contact between an external bias and measurement circuit 154 and nanotube probes. Finally, sealed connections 156 are provided for enabling the application of an external circuit 158 for electrically biasing the two liquid compartments without leakage of the liquids out of their compartments.

With this arrangement, it can be preferred that the contact area of liquid to the cis, i.e., top, side of the support structure should be as small as possible, e.g., less than about 1,000 $\mu m^2$, to minimize the capacitance of the system. The channels 136 for delivery of liquid to the cis side of the nanopore are preferably configured for delivery to within less than about 300 $\mu m$ of the nanopore. The channels preferably are less than about 200 $\mu m$ in diameter, and are connected to tubing that is preferably less than about 200 $\mu m$ in diameter, in order to minimize the sample volume needed to fill the liquid compartment without air bubbles.

Turning now to more specifics of processes for producing the molecular characterization devices of the invention, a nanopore can be formed in a support structure in any suitable method. Where the support structure is provided as a membrane, the membrane is formed in the conventional manner, e.g., as taught in U.S. Pat. No. 6,627,067, incorporated by reference above. Then an initial aperture is formed in the membrane, for subsequent processing to produce a final, smaller nanopore diameter. In one technique in accordance with the invention, an initial aperture is formed in a membrane by, e.g., ion beam milling, electron beam etching, plasma etching, wet etching, or other selected technique for forming an aperture through the thickness of the membrane. Then the initial aperture diameter is reduced through a selected process. In one example technique, the aperture diameter is reduced to that of a nanopore through a process of ion beam sculpting, as taught in U.S. Patent Application Publication US2005/0006224, Golovchenko et al, "Pulsed Ion Beam Control of Solid State Features," the entirety of which is hereby incorporated by reference.

In the process of forming a nanopore, the surface of the nanopore, along the nanopore length, may be processed to minimize or inhibit adsorption of ssDNA on the nanopore surface as the DNA translocates through the nanopore. It is known that various biomolecules, such as ssDNA, will tend to bind on either hydrophilic and cationic surfaces, via the anionic backbone of the strand, or will tend to bind on hydrophobic surfaces via the nucleotides. It can therefore be preferred in the process of fabricating the nanotube-articulated nanopore configuration to either provide the support structure, in which the nanopore is formed, of a material that is inert to a molecule of interest, e.g., ssDNA, or to coat the nanopore and support structure with a material layer that is inert to the molecule of interest. Thus, it can be preferred to provide an insulating surface layer on the nanopore that will have a neutral surface charge when in contact with the molecule-bearing electrolytic solution. If the molecule-bearing solution is at or near pH=7, aluminium oxide is an ideal coating material. If the molecule-bearing solution is pH 9, hafnium oxide can instead be preferred, as it indefinitely withstands a high pH environment without degradation.

Where the nanopore is to be coated with a selected material layer, the process of atomic layer deposition (ALD) can be preferred as a deposition technique. ALD is particularly advantageous in conjunction with nanopore fabrication because it can modify the electrical charge as well as material properties of a surface while yielding highly conformal step coverage of many different materials, even over high-aspect-ratio structures, with precise, single-Ångström thickness control. In addition the ALD process can be used for controlling the pore size and for insulating the nanotube electrodes away from their molecular sensing regions, as described in detail below.

Where aluminum oxide is the selected coating layer material, such can be deposited by, e.g., atomic layer deposition (ALD) in a manner that enables monolayer deposition control, e.g., as taught in U.S. Patent Application Publication No. US2005/0241933, Branton et al., "Material Deposition Techniques for Control of Solid State Aperture Surface Properties," the entirety of which is hereby incorporated by reference.

In an example process for producing a film by ALD on a nanopore, in a first process step, the surfaces of the structure on which the film is to be deposited are prepared to react with a selected molecular precursor or precursors. For many applications, a metal precursor is employed for the ALD process, e.g., an ALD metal precursor can be provided as $ML_x$, where M=Al, Ha, Mg, W, Ta, Si, or other metal, and L=$CH_3$, Cl, F, $C_4H_9$, or other atomic or molecular ligand that produces a volatile molecule. For example, for deposition of an $Al_2O_3$ layer on a nanopore the structure is first exposed to, e.g., UV/ozone, immediately prior to ALD deposition, in order to generate hydroxylated surfaces that are highly reactive to a metal precursor for forming the alumina layer.

Once hydroxyl groups are produced on the structure surface, a precursor, e.g., the metal precursor trimethylaluminum [$Al(CH_3)_3$] (TMA) for deposition of alumina, can be employed to react with the produced hydroxyls at the surface, i.e., a gaseous precursor including $Al(CH_3)_3$ molecules is provided to react with the surface —OH sites. This reaction produces volatile $CH_4$ gas molecules and forms $Al(OH)_2(CH_3)$ or $Al(OH)(CH_3)_2$ at the initial —OH sites. For such an alumina formation process a suitable reaction zone temperature is between about 200° C. and about 300° C.

The $Al(CH_3)_3$ reaction with the hydroxyl groups is self-terminating in that during the reaction the initial surface ligands, —OH, are consumed and the surface becomes populated with L ligands that cannot further react with the metal precursor. This self-limiting reaction process can result in deposition of less than or more than a monolayer of material on the structure and pore surfaces. In a next ALD process step, any remaining unreacted $Al(CH_3)_3$ precursor and the produced $CH_4$ gas is flushed from the reaction chamber, e.g., with dry nitrogen or other suitable carrier gas. In a next process step, water vapor is admitted into the reaction chamber to cause the surface of the deposited layer to be reactive with the selected precursor. In the current alumina deposition example, the water vapor is provided to react with exposed $CH_3$ groups. The reaction of water vapor with available $CH_3$ groups liberates $CH_4$ gas and attaches —OH groups at each —$CH_3$ site, resulting in a newly hydroxylated surface. This hydroxylation process self terminates when all —$CH_3$ sites have reacted with the water vapor. During this process, adjacent —$Al(OH)_2$ sites cross-link to produce water molecules and a linked Al—O—Al network.

In a next process step, the remaining water vapor and the liberated $CH_4$ groups are exhausted, e.g., with a nitrogen flushing step in the manner described above. This completes one ALD reaction cycle, producing a layer of alumina on the structure and pore surfaces and sidewalls. The deposited layer can then react with a next cycle of water vapor followed by $Al(CH_3)_3$ admitted into the reaction chamber for reaction. The duration of each process step in one ALD reaction cycle is selected to enable sufficient reaction time without providing excessive precursor or exhaust. For example, in the example alumina deposition process, one ALD cycle can be employed as 1 s flow of the metal precursor vapor into the reaction chamber followed by 5 s nitrogen purge and then 1 s flow of water vapor followed by another 5 s nitrogen purge. A layer of alumina, which can be, e.g., about ⅓ of a monolayer thick, is formed after each such cycle.

With these process conditions for ALD of an alumina layer, it was experimentally determined that the deposition rate of $Al_2O_3$ is 0.99±0.12 Å per reaction cycle, independent of the total number of cycles. This deposition rate was verified over 20-500 cycles. Thus, starting with a 2 nm-diameter nanopore, the nanopore diameter can be reduced to 1 nm by 5 cycles of the $Al_2O_3$ deposition process with an error of only about ±1.2 Å.

In an alternative technique provided by the invention, a Teflon-like layer can be deposited on the surface of the nanopore and the support structure, e.g., as taught in U.S. Pat. No. 5,888,591, Gleason et al., "Chemical Vapor Deposition of Fluorocarbon Polymer Thin Films," hereby incorporated by reference.

To articulate solid state nanopores with nanotube probes, it can be preferred to integrate nanotubes with the nanopore in a selected support structure. In one fabrication technique, carbon nanotubes are synthesized directly on a support structure of interest, as taught in U.S. Pat. No. 7,466,069, issued Dec. 16, 2008, to Golovchenko et al., for "Carbon Nanotube Device Fabrication," the entirety of which is hereby incorporated by reference.

In this technique, precise control of catalyst properties, and correspondingly precise control of nanotube growth are enabled, such that single-walled nanotubes oriented horizontally, parallel to a support surface, are selectively synthesized for configuring the nanotube probes. In this process, the catalyst layer is formed by vapor deposition of a solid catalyst material, by sputtering, molecular beam epitaxy, sol gel formation, E-beam evaporation, thermal evaporation, or other selected vapor deposition process on the support structure. Whatever vapor deposition process is selected, it preferably is controlled to enable very low coverage of the vapor-deposited film, such that no more than several monolayers of the selected catalyst material are deposited on the membrane or support substrate.

In one example vapor deposition process, thermal evaporation of Fe using a tungsten boat spot welded with Fe foil can be carried out under vacuum conditions, e.g., at a pressure of about $10^{-5}$ or $10^{-6}$ Torr, to produce a Fe catalyst layer of selected thickness. Whatever catalyst material and vapor deposition process is employed, it is preferred that the resulting catalyst layer thickness be less than about 2 nm, or considered another way, it is preferred that the catalyst layer be characterized by a layer coverage of about $8 \times 10^{15}$ atoms/$cm^2$ or less. It is understood that as the catalyst layer thickness is increased, the diameter of nanotubes that are horizontally synthesized from the catalyst layer correspondingly increases, and above a threshold catalyst layer thickness, multi-walled, rather than single-walled, horizontal nanotubes are formed. A thin catalyst layer, e.g., of 2 nm in thickness or less, is understood to be adequate for predictably and reliably forming single-walled nanotubes.

In one example fabrication sequence, contact pads are first formed on the selected support structure in the conventional manner, e.g., as a layer of palladium for forming an ohmic contact with the nanotube probes. The contact pads are formed near to where the nanopore is to be located. A nanotube catalyst layer is then formed on top of the metal contact pad layer or layers. Then using conventional lift-off techniques, a patterned photoresist layer is removed, resulting in patterned catalyst/electrode regions. This technique can be particularly advantageous because it enables patterning of both nanotube probe contact pads and catalyst layers in a single step. For applications in which it is acceptable for the extent of catalyst regions to coincide with that of nanotube probe contact pads, this process can therefore be preferred.

If for a given application, it is preferred that the catalyst regions do not fully cover the contact pads, then an additional lithographic and etch sequence can be carried out to remove catalyst material from portions of the contact layer. In one example process, the catalyst layer is masked with, e.g., a patterned photoresist layer, exposing regions of the catalyst layer that are to be removed. A dry etch process, e.g., plasma etching, ion beam etching, or other technique, is then employed to remove the unwanted catalyst layer regions. It is recognized that many catalyst layer etch processes may not be significantly selective in etching the catalyst material over the underlying metal electrode material. It therefore can be preferred that the catalyst etch process be controlled as a timed process or with other controls to ensure that the integrity of the metal contact pad material is maintained.

In an alternate process, the catalyst layer can be patterned and etched in a sequence of steps separate from that employed for the nanotube probe contact pad layer. For example, the contact pad layer can be patterned by, e.g., a conventional lift-off process as just described, and then the catalyst layer deposited and patterned by a second separate lift-off process. In this scenario, a photoresist layer is formed over the produced contact pads and patterned to expose regions of the contact pads at which it is desired to provide a region of nanotube catalyst layer. The catalyst layer is then blanket-deposited, preferably by a selected vapor deposition process like that described above. Lift-off of the photoresist layer is then carried out to remove portions of the catalyst layer, resulting in a patterned catalyst region atop the contact pads.

It is not required that the catalyst layer be patterned by a lift-off process; instead, the catalyst layer can be blanket-deposited on the contact pads and then etched, e.g., by lithographic patterning of a photoresist layer applied on top of the catalyst layer and patterned to define distinct catalyst islands. Etching of the catalyst regions exposed through the photoresist pattern can then be carried out in the conventional manner. This approach, like the catalyst lift-off approach, has the advantage of enabling precise formation of catalyst islands that do not necessarily extend across an entire electrode contact pad, and therefore that more precisely define the location of nanotube synthesis.

Whatever process sequence is employed to produce contact pads and catalyst regions, it can be preferred in accordance with the invention to extend the contact pad and catalyst regions across an intended aperture location, such that production of an aperture through the contact pad and catalyst layers results in self alignment of the contact pads and catalyst regions with edges of the aperture. This results in production of two contact pads that are separated by the aperture. The catalyst layer regions can also abut the aperture edge and not extend across the expanse of the contact pads. Such a condition can be produced by the various catalyst layer etch sequences just described. Whatever catalyst pattern is desired, it is preferably produced by a lithographic process that enables precise definition of the location and extent of catalyst regions. This lithographic catalyst definition, in combination with vapor deposition of a thin catalyst layer, enables precise nanotube synthesis.

This lithographic definition of the catalyst regions does not require etching of the catalyst layer. For example a blanket deposition of catalyst layer can be carried out in the manner described above, and then a capping layer can be deposited and patterned. The capping layer pattern exposes regions of the catalyst layer at which it is desired to synthesize nanotubes, with the remainder of the catalyst layer being covered to inhibit nanotube synthesis. With this configuration, the catalyst layer is not itself etched, but through lithography the precise location of catalyst exposure for nanotube synthesis is accomplished.

Once the catalyst layer regions are formed at selected sites on the contact pads, an aperture is formed through the membrane or other support structure on which nanotubes are to be provided. In one example process, focused ion beam milling of the catalyst, contact pad, and membrane materials is carried out directly, in the manner described previously, to enable self alignment of the various layers with the aperture. The resulting structure provides an aperture with contact pads and catalyst regions in alignment. Alternatively, lithographic patterning of each layer to be etched can be carried out in sequence, with one or more layers etched together as possible by a given etch recipe. Furthermore, a plurality of apertures can be formed in a given substrate, membrane, or other support structure, in arrays or other configuration suitable for a given application.

Once a selected aperture or apertures are produced, nanotube synthesis can be carried out on the substrate or membrane. The nanotube synthesis is particularly carried out to produce one or more nanotubes bridging each aperture to connect to edges of the aperture or to contact pads. In one example synthesis process, nanotube growth is carried out in a suitable system, e.g., a furnace system. A substrate on which nanotube growth is desired is loaded into the furnace system and the temperature of the system is raised to the desired growth temperature, which can be, e.g., between about 600° C.-1500° C., and preferably is about 900° C. During the temperature ramp, it can be preferred to provide a flow of an inert gas, e.g., argon, to suppress oxidation of the contact pad material, catalyst material, membrane and/or substrate material, and other materials included in the configuration.

When the desired synthesis temperature is reached, the gas flow is switched to a hydrocarbon gas, e.g., a methane gas flow. The methane gas flow is preferably maintained at between about 100 sccm and about 400 sccm, with a flow rate of about 200 sccm preferred. With this relatively low gas flow, it is found in accordance with the invention that amorphous carbon formation on and around synthesized nanotubes and the substrate area is substantially inhibited. As a result, in accordance with the invention there is no need for inclusion of hydrogen or other gas flow in addition to the methane to inhibit amorphous carbon formation. It is understood in accordance with the invention that the influence of gas flow direction on the orientation of nanotubes as they are synthesized is negligible, and therefore that no particular orientation of substrates with respect to gas flow is required.

The methane gas flow exposure of the catalyst material can be carried out for any duration required for a given application to produce nanotubes of selected diameter and quantity. For many applications, it can be preferred to carry out the methane gas flow exposure for 10 minutes or less to repeatably synthesize single-walled nanotubes. If such is not a requirement, the gas flow can be continued for any selected duration corresponding to a desired nanotube wall thickness. It is found, however, that minimization of nanotube synthesis time can be preferred in that such reduces the production of amorphous carbon on the nanotubes and surrounding structures.

With this process, nanotubes can be selectively synthesized on the surface of a support structure at or near to the location of an aperture to be formed into a nanopore in the manner described below. It is to be recognized that electrical characterization of synthesized nanotubes can be preferable for ensuring that a selected nanotube provides the requisite electrical properties for functioning as a probe. A nanotube with a desired diameter and electrical properties that has been synthesized near to a position at a nanopore where the nanotube is desired can then be manually pushed into position by, e.g., an AFM cantilever tip.

For applications in which a nanotube is to be mounted to the tip of an actuating structure, e.g., the tip of an AFM cantilever beam, for translocating a tip-mounted DNA-nanopore complex through a nanopore, the invention provides a technique for producing a selected nanotube length on the mounting tip, as taught in U.S. Ser. No. 11/008,402, Golovchenko et al., "Patterning by Energetically-Stimulated Local Removal of Solid-Condensed-Gas Layers and Solid State Chemical Reactions Produced With Such Layers," U.S. patent application publication No. US 2007/0262050, the entirety of which is hereby incorporated by reference. This technique can also be applied for producing a desired nanotube length for operation as a nanotube probe or in a DNA-nanotube hybrid complex.

In a first step of such a process sequence, a nanotube is provided on a nanotube holder that can be provided on a structure holder enabling electrical and thermal connections for control of the electrical and thermal state of a structure. Preferably the nanotube holder can be mated with the structure holder such that thermal and electrical connection can be made to the nanotube. The nanotube holder can be provided as, e.g., an AFM tip, or as another suitable, mechanically rigid structure, such as a cantilever structure, on which a nanotube can be mounted and actuated for controlled translocation through a nanopore, if such is the application to be addressed.

The nanotube can be positioned on the nanotube holder in a number of ways. For many applications, it can be preferred to grow the nanotube in situ on the holder following the technique described above. But any suitable carbon nanotube synthesis technique can be employed for locating the carbon nanotube on the nanotube holder as the nanotube is grown. Alternatively, carbon nanotubes can be synthesized at a location other than the nanotube holder and then transferred or deposited to the holder. Alternatively, nanotubes can be grown vertically from a substrate in the conventional manner and then picked up directly onto a holder by bringing a holder into contact with a nanotube at a point along the length of the tube. A rigid attachment of the nanotube to the holder can be produced by, e.g., directing an electron beam to the holder to build up a carbon residue that can act as a gluing mechanism between the holder and the nanotube. It is recognized that these attachment techniques can be challenging; therefore, the in situ growth of a nanotube directly on a holder of interest is preferred.

Once a nanotube is located on a nanotube holder, the nanotube and holder are positioned on a structure holder in a processing chamber. A solid ice condensate layer is then formed on the nanotube by exposing the nanotube to water vapor at a nanotube temperature of less than about 130 K and a local pressure of less than about $10^{-4}$ T. Under these conditions, a solid ice condensate masking layer having a thickness of as much as 1 µm can be controllably deposited on the nanotube. It is found that solid ice condensate masking layer formation can be quite directional on a three-dimensional structure such as a nanotube and therefore that the proximity of the vapor injector at its site on the process chamber to the nanotube holder location is preferably considered. The masking layer formation can be monitored in situ by, e.g., SEM imaging of the nanotube as the vapor condensation process progresses.

Once a masking layer is formed on a nanotube, then an energetic beam is directed to a location on the masking layer which corresponds to that point along the nanotube that is to be cut for shortening the nanotube. An SEM or other imaging system and technique can be employed for imaging the nanotube to determine its starting length and to identify the point at which the tube is to be cut for reducing the tube length. An energetic beam, e.g., a 3 KeV, 50 pA electron beam, or an ion beam, is then directed to that point to locally remove the solid condensate masking layer just at the location desired for nanotube cutting.

Once local removal of the solid condensate masking layer is complete, thereby exposing a location of the underlying nanotube, then the nanotube itself is cut. Here an energetic beam is directed to the nanotube at the section along the nanotube length that is exposed by the local removal of the solid condensate layer, to cut the nanotube to a desired length. The energetic beam employed to cut the nanotube can be the same as or distinct from the energetic beam employed to locally remove the solid condensate masking layer. Whatever nanotube cutting beam species is employed, the solid condensate masking layer acts to protect the nanotube and prevent it from bending or moving away from the energetic beam as the cutting beam species is directed at the exposed nanotube section and focused at that exposed section. The solid condensate masking layer further acts to protect and keep the nanotube rigid as the nanotube is cut at the exposed section. As a result, a highly focused cutting beam species is not required; the linewidth of the locally removed solid condensate masking layer can be employed to set the resolution of the nanotube cutting process.

In an example of such a scenario, an electron beam can be employed to locally remove a region of a solid ice condensate masking layer on a carbon nanotube, e.g., the 3 KeV, 50 pA beam described above can be employed to locally remove an ice masking layer formed on a nanotube at a temperature of 128 K and a pressure of $10^{-4}$ T. Then an ion beam can be employed to cut the nanotube at the location of the nanotube at which the ice masking layer was locally removed. For example, a Ga$^+$ ion beam of 30 KeV in energy and an amperage of 10 pA can be employed for cutting the nanotube. Here the less focused ion beam is employed to cut the nanotube, with the solid ice condensate layer protecting the nanotube.

Once the nanotube is cut, the solid condensate masking layer can be removed. For many applications, it can be preferred that the masking layer be removed by conversion from the solid phase back to the vapor phase. Such vaporization minimizes both the formation of residue on the nanotube and possible damage to the nanotube. In one example process the ice condensate masking layer is sublimed by increasing the temperature of the nanotube to a temperature sufficient for sublimation at process pressures of interest. For example, at a pressure of about $10^{-4}$ T, a temperature of at least about 180 K enables sublimation of an ice condensate layer. Such is found to result in complete removal of the ice condensate layer to the vapor phase, substantially without residue or harm to the easily bent or damaged nanotube. The condensate masking layer can be removed by any suitable process as explained previously, including wet chemistries as well as plasma or other vapor processes. With this removal step, a nanotube of a selected length is produced.

The various fabrication processes just described can be employed as-required for producing a selected molecular analysis device configuration. The following examples demonstrate fabrication techniques for producing a range of device configurations.

Example I

Figure 8A:
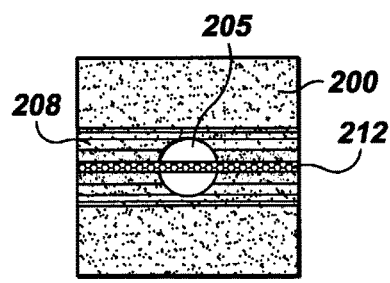
FIGS. 8A-8F are schematic cross-sectional views showing fabrication steps in an example process for producing a molecular characterization device.
Figure 8C:
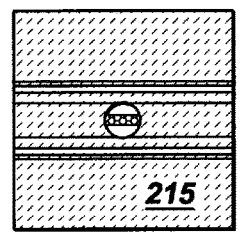
Figure 8E:
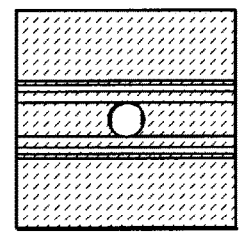
Figure 8B:
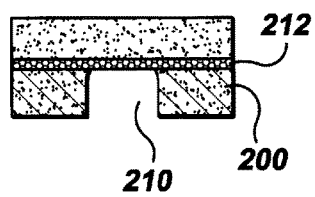

Referring to FIGS. 8A-8B, in a first example fabrication sequence for producing an electronic molecular analysis device in accordance with the invention, a support structure 200 is provided, e.g., a silicon nitride membrane of about 200 nm in thickness, in the conventional manner, and as taught in U.S. Patent Application Publication US2005/0006224, Golovchenko et al., "Pulsed Ion Beam Control of Solid State Features." As shown in the top-down planar view of FIG. 8A, the membrane is provided with a starting aperture 205 by, e.g., electron beam etching, ion beam milling, wet etching, plasma etching, ion beam sculpting, or other suitable process.

In one example, the starting aperture is generally circular, having a diameter of between about, e.g., 50 nm and 100 nm. As depicted in the planar view of FIG. 8A and the side face view of FIG. 8B, the support structure 200 is provided with an upper trench, or groove 208 in the top surface of the structure and a lower trench 210 in the bottom surface of the structure. The upper and lower trenches 208, 210 are orthogonal to each other, and the aperture 205 is formed at the intersection of the two trenches. This orientation enables self-alignment for the nanotube probe positioning, as explained below.

The upper and lower trenches can be produced by using a focused ion beam process or by standard patterned masking and etching procedures. For many applications, the trenches can be formed as less than about 100 nm in width and about ½ as deep as the thickness of the support structure membrane. The exact depth of a trench produced by a given procedure can be determined by testing a series of stepwise increasingly deep trenches; e.g., for a 200 nm-thick membrane, trench depths of 50 nm, 70 nm, 90 nm, 110 nm, etc., to calibrate the procedure for a given batch of silicon nitride membranes. The depth of the trench that produces the desired diameter starting nanopore, e.g., between about 50 nm and about 100 nm, can then be routinely used in an open loop fashion for the subsequent fabrications.

With this configuration of the support structure complete, a nanotube 212 is then provided in the upper trench 208, across the aperture 205. The nanotube 212 can be disposed at the aperture location in the trench by in situ synthesis of the nanotube at the aperture, or by positioning of a free nanotube at the aperture. In situ synthesis of the nanotube can be carried out in the manner described above, e.g., with a catalyst deposited and patterned in the upper trench followed by CVD nanotube synthesis. Alternatively, pre-synthesized nanotubes provided in a non-aqueous solution can be dispensed onto the surface of the support structure and a selected nanotube mechanically transported to the trench.

This mechanical transporting of a selected nanotube has been experimentally verified to enable precise movement and positioning to a prespecified location. In one technique for such movement and positioning, an AFM tip is employed to roll a nanotube across a surface and down into a trench to the location of the aperture. Note that for clarity, the features in FIG. 8 are not shown to scale. The nanotube diameter is typically many times smaller than the trench depth and width. In addition, surface attraction effects, such as van der Waals forces, cause a nanotube to tend to remain in place on a surface. As a result, a nanotube can be well-controlled by an AFM tip and rolled across a surface and down the wall of a trench into a desired position at the location of an aperture.

The selected nanotube can be electrically contacted by contact pads formed prior to synthesis, as described above, or subsequently electrically contacted by forming, e.g., palladium contact pads that are in turn connected to larger gold contact pads that connect to off-chip circuitry by conventional methods, e.g., as in Javey, A., et al. Nature 424: 654 (2003) and Javey, A. et al. Nano Letters 4:447 (2004). In this process, palladium is evaporated onto the nanotubes, through a mask, at the desired location near to the aperture perimeter.

Figure 8D:
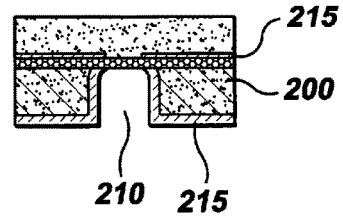

Referring to FIGS. 8C-8D, in a next process step, a selected coating is deposited on the nanotube-support structure assembly. A particularly well-suited deposition technique is the atomic layer deposition (ALD) process described above. The ALD process is particularly well-suited because the deposition of material is strictly dependent on the chemical interaction between a gas-phase molecule and hydroxyl or other functional groups accessible at the surface of the material on which a coating is to be deposited. Absent such functional groups, no deposition of the gas-phase molecules occur. Carbon nanotubes as-synthesized do not in general possess functionalized surfaces that provide the requisite hydroxyl or other functional groups for deposition of the gas phase material. Thus, if an insulating material such as aluminum oxide or hafnium oxide is deposited by ALD on a device configuration that includes silicon, silicon nitride and nanotubes, aluminum oxide or hafnium oxide will grow uniformly by chemical reaction at the surfaces of all of these structures, including the newly formed aluminum oxide or hafnium oxide surfaces, but will not grow from the carbon nanotube surfaces which, as grown, do not have functional groups such as hydroxyl groups at their surface. This condition can be exploited to enable site-specific deposition of such materials on the support structure but not directly on, from, or over the unsupported nanotube, e.g., not on or over a region of a nanotube that is suspended over a pore or void. Even if material deposition does occur on the nanotube, the following fabrication sequence can be employed.

In one such scenario, a selected number of ALD cycles are carried out, in the manner described above, depositing material on all surfaces of the support structure 200 including the walls of the aperture and the trenches 210. The deposition of the selected material extends over and may cover regions of a nanotube that are supported by, or proximal to any of the silicon nitride or newly grown ALD material, but does not itself originate from the nanotube surface. As the material deposition is continued, the build up of deposited material at the aperture reduces the extent of the aperture. Accordingly, the deposition process is continued until a selected final nanopore diameter is produced, e.g., a diameter of between about 2 nm and about 10 nm. Due to the very precise nature of the ALD process, the material thickness produced by each ALD cycle can be precisely characterized for a given support structure and nanotube arrangement and dimensions and controlled to achieve a selected final nanopore diameter with the upper side of the nanotube coated. For example, with a starting aperture of 50 nm, 220 ALD cycles, each adding a layer 1A-thick, would produce a final pore of 6 nm in diameter.

Figure 8F:
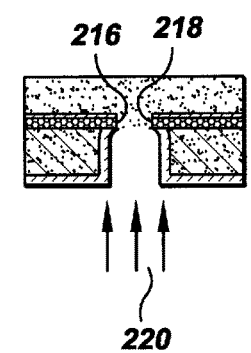

Once a final nanopore diameter is achieved by the ALD process, the nanotube probe configuration is produced at the perimeter of the nanopore. Referring to FIGS. 8E-8F, this configuration is achieved by cutting through the nanotube that lies exposed across the final nanopore to produce two nanotube ends 216, 218 that abut on the nanopore perimeter. In one example nanotube cutting technique, an energetic beam 220, e.g., a high-energy electron beam or preferably, an ion beam, is directed through the nanopore, from the bottom or top of the support structure. The energetic beam removes the exposed unprotected nanotube material from the nanopore, while the aluminum oxide or other ALD coating protects the ALD covered regions of the nanotube and support structure from the beam species. Thus, the nanopore acts as an etch mask, exposing the bare nanotube to be removed from across the nanopore, while the remainder of the structure is protected by the ALD coating that is absent within the diameter of the final nanopore. Once the bare nanotube is removed from across the final nanopore, a functional molecular characterization device like that of FIG. 1A is produced, having the ends of nanotube probes abutting a nanopore perimeter.

Example II

Figure 9J:
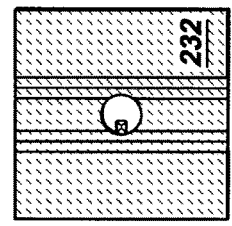
FIGS. 9A-9L are schematic cross-sectional views showing fabrication steps in a further example process for producing a molecular characterization device.
Figure 9G:
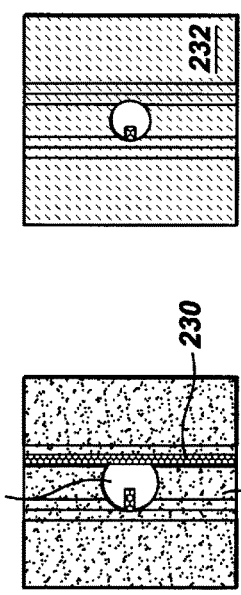
Figure 9D:
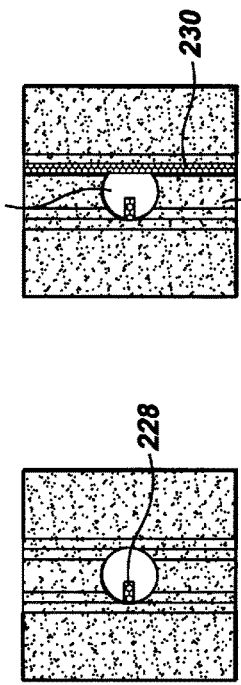
Figure 9A:
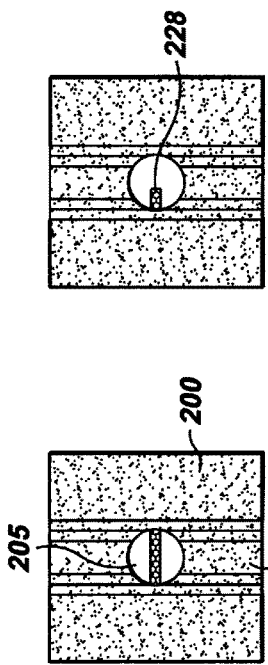
Figure 9K:
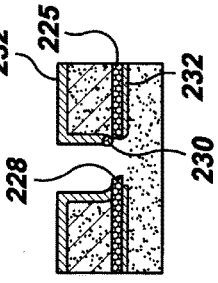
Figure 9H:
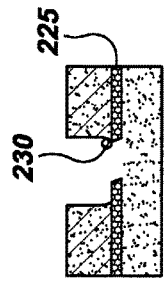
Figure 9E:
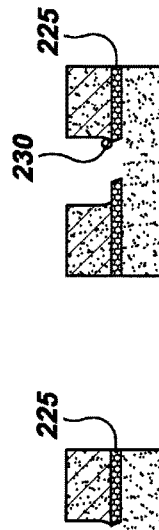
Figure 9B:
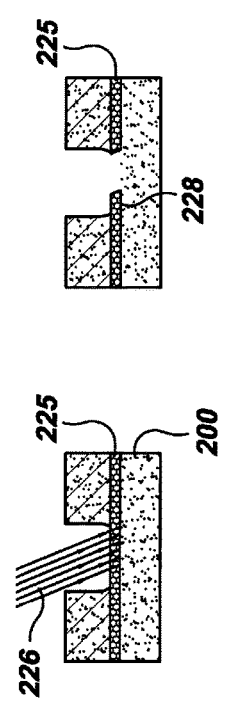
Figure 9L:
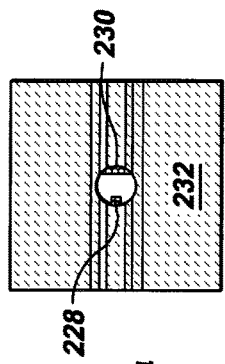
Figure 9I:
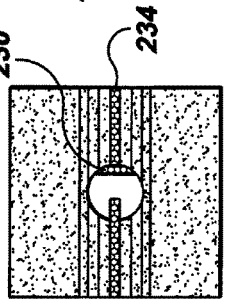
Figure 9F:
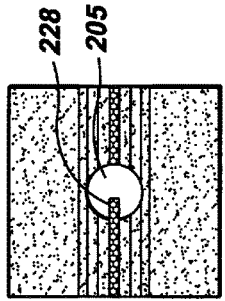
Figure 9C:
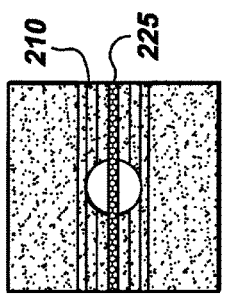

Referring now to FIGS. 9A-9C, in a further fabrication sequence for producing an electronic molecular analysis device, a support structure 200 such as a silicon nitride membrane is provided with an aperture 205 in the manner of Example I. Orthogonal trenches 208, 210 are provided in the top and bottom surfaces, respectively, of the support structure, with the aperture located at the intersection of the trenches as in Example I.

With this configuration in place, a nanotube 225 is positioned in the lower trench 225 in the manner of Example I. FIG. 9A depicts the upper planar surface of the structure, showing the nanotube across the aperture, while FIG. 9C depicts the bottom planar surface of the structure, showing the nanotube in the bottom trench across the aperture.

As shown in the end face view of FIG. 9B, in a next process step, an energetic beam 226, e.g., an ion beam, is then directed, from the upper side of the membrane, through the aperture at an angle selected to cut the nanotube at the position that will leave it abutting the final nanopore perimeter at the end of the fabrication sequence, e.g., at an angle of about 64 degrees, specifically for the particular geometry shown; for a given geometry, a corresponding angle is to be determined. This angled beam impinges and removes that portion of the nanotube in the aperture that is in the path of the beam. The resulting structure is shown in FIGS. 9D-F. The portion 228 of the nanotube 225 in the aperture that was not in the path of the ion beam remains protruding into the aperture.

Referring to FIGS. 9G-I, in a next process step, a second nanotube 230 is then provided in the upper trench 208 such that it extends off-center across the aperture. This second nanotube 230 can be synthesized in situ at the site of the trench or mechanically positioned in the trench and if desired, off-center across the aperture, as in Example I above. In either case, if desired, the second nanotube 230 is not positioned in the center of the aperture but instead, as shown in FIGS. 9G-I, at a point in the trench such that its side will just abut the perimeter of the final nanopore.

With the second nanotube in position, then as shown in FIGS. 9J-L, a selected material is deposited on the support structure, e.g., by ALD in the manner described above. As in Example I above, the deposited material forms a layer 232 on all of the surfaces except those of the unsupported nanotube, resulting in the structure shown in FIG. 9J.

As shown in FIG. 9K, as the material deposition proceeds, the aperture diameter is reduced by the deposited material. The build up of deposited material also increasingly covers the protruding portion 228 of the first nanotube 225 and the upper surface of the second nanotube 230. The material deposition is continued until a selected nanopore diameter is achieved, with the edge of the protruding nanotube portion 228 and the second nanotube 230 located at the final nanopore perimeter. To enable this condition, the selected deposition process, e.g., ALD, is characterized for a given support and nanotube arrangement, to ensure that a desired nanopore diameter is achieved at the point in deposition process at which the protruding nanotube portion 228 and the second nanotube 230 are covered by the material except at a region just at the nanopore perimeter, as shown in FIG. 9L.

With this deposition complete, a fully functional molecular characterization device is produced having the arrangement of FIGS. 2A-2C. Referring back to FIG. 9l, the nanotube portion 234 of the first nanotube 225, opposite the protruding portion 228 is not electrically connected and does not form part of either circuit 28, 52 shown in FIG. 2B. The protruding nanotube portion 228 and the second nanotube 230 form two nanotube probes, in an end orientation and a side orientation, respectively, connected in the two circuits for control and analysis of DNA translocated through the nanopore.

Example III

The fabrication sequence of Example II can be extended to produce the molecular analysis device of FIGS. 3A-C and FIG. 4A described above. Referring to FIGS. 10A-C, in this extended process, a nanotube 225 is provided in the bottom trench 210 of a support membrane 200 having an aperture 205 at the intersection of the bottom trench 210 with an upper trench 208 as in FIGS. 9A-C. An energetic beam is then employed as in Example II and FIG. 9B to remove a portion of the nanotube 225, resulting in a protrusion 228 of the nanotube into the aperture, as in FIGS. 10A-C. A second nanotube 230 is then positioned, as in FIGS. 9G-I and 10D-F, at the perimeter of the aperture if desired, in the upper trench 208 of the support structure.

Referring to FIGS. 10G-I, a third nanotube 234 is then disposed on the upper surface of the support structure 200, orthogonal to the second nanotube 230 in the upper trench 208 and at a position on the perimeter of the aperture. This third nanotube 234 can be synthesized in situ or manually positioned at the selected location, both as described above.

In a final process step, referring to FIGS. 10J-L, a selected material is deposited on the support structure, e.g., by ALD in the manner described above. The deposited material forms a layer 236 on the upper surface of the support structure and the upper trench, and does not originate at the second nanotube 230, as shown in FIG. 9J. The third nanotube 234 remains uncoated in the region of the aperture due to the un-functionalized nanotube surface and the lack of membrane material around the third nanotube in the aperture. As a result, the third nanotube remains exposed at the perimeter of the aperture.

The deposited material layer 232 also covers the bottom surface of the support structure, as shown in FIG. 10L. As shown in FIG. 10K, as the material deposition proceeds, the aperture diameter is reduced by the deposited material. The build up of deposited material also increasingly covers the protruding portion 228 of the first nanotube 225 and the upper surface of the second nanotube 230. The material deposition is continued until a selected nanopore diameter is achieved, with the edge of the protruding nanotube portion 228 and the second nanotube 230 located at the final nanopore perimeter. To enable this condition, the selected deposition process, e.g., ALD, is characterized for a given support and nanotube arrangement, to ensure that a desired nanopore diameter is achieved at the point in deposition process at which the protruding nanotube portion 228 and the second nanotube 230 are covered by the material except at a region just at the nanopore perimeter, as shown in FIG. 10L.

With the deposition complete, a nanopore having a side-oriented translocation control nanotube 234, an end-oriented nanotube probe 228, and a side-oriented nanotube probe 230 are provided. The fabrication sequence of this example results in a translocation control nanotube 234 that is orthogonal to the side-oriented nanotube probe 230. In FIG. 4A a device arrangement is shown in which a translocation control nanotube 65 is parallel to a side-oriented nanotube probe 50. Either arrangement can be employed in accordance with the invention, and this example demonstrates that a range of configurations can be obtained with selected fabrication sequences.

If it is desired to employ two end-oriented nanotube probes with a translocation control nanotube as in the arrangement of FIGS. 3A-3C, then the fabrication sequences of Examples I and III can be combined. Prior to the deposition and nanotube removal steps of FIGS. 8C-8F, the third nanotube 234 in FIGS. 10G-I can be provided on the top surface of the support structure; the deposition and etch steps can then proceed to produce the structure of FIGS. 3A-3C.

Example IV

In a further fabrication sequence for producing a molecular analysis device in accordance with the invention, there is provided an end-oriented nanotube probe and a side-oriented nanotube probe disposed along the length of a nanopore, as in the arrangement of FIG. 4B. Referring to FIGS. 11A-B, in a first step of this fabrication sequence, a relatively thick support structure, e.g., a thick silicon nitride membrane, is provided. For example, a nitride membrane having a thickness of, e.g., about 800 nm can here be employed. A series of apertures are provided in the membrane in the manner described above. FIG. 11A is a planar top down view of a region of a thick membrane 240 in which two apertures 242, 244 are provided. FIG. 11B is a side end face view of the membrane structure of FIG. 11A.

In a next process step, shown in FIGS. 11C-D, an energetic beam 246, e.g., an ion beam, or standard lithographic processing, is used to remove, e.g., about one-third of the membrane material from the top of the membrane such that a new membrane surface orthogonal to the original membrane surface intersects the diameter of the original membrane apertures. This process is then repeated at the bottom of the membrane to remove, e.g., about one-third of the membrane material from the bottom of the membrane, again creating a new membrane surface orthogonal to the original membrane surface and which intersects the diameter of the original membrane apertures. As a result, a portion of the original membrane is now only one-third as thick as the original membrane and the other portion of the original membrane remains at its original thickness. Because the edge of the removed portions of the membrane from the top and bottom surface extend through the diameters of the original apertures, longitudinal grooves 248, 250 are exposed along the length of the newly created membrane surfaces that are orthogonal to the original membrane surfaces. These groves extend as apertures through the thickness of the residual membrane whose surface is parallel to the original membrane surfaces.

In a next process step, referring to FIGS. 11E-F, nanotubes are synthesized in situ on the membrane structure, in the manner described above. Catalyst material is deposited and patterned adjacent to and in the groves on one of the newly created orthogonal membrane surfaces and on the residual membrane whose surface is parallel to the original membrane surfaces at locations adjacent to the apertures. Nanotubes are then synthesized on the membrane structure. FIGS. 11E-F depict a number of synthesized nanotubes, e.g., 252, 254, 256, 258 on the membrane support structure. Given a number of apertures provided in the membrane structure, it is recognized that at least one synthesized nanotube can be expected to grow along a grove and through an aperture through the thickness of the residual membrane whose surface is parallel to the original membrane surface, as with the nanotube 256 shown in the aperture 242 of the membrane in FIG. 11E.

With identification of an aperture 242 though which a nanotube 256 has been synthesized, then in a next process step, shown in FIGS. 11G-H, a selected second nanotube 260 is manually positioned relative to the aperture 242 such that an end portion 262 of the second nanotube 260 protrudes well into the aperture 242. Alternatively, this second nanotube could be positioned such that a long side of the nanotube runs off-center across the aperture, as in Example I above. In this case, the second nanotube is not positioned in the center of the aperture but instead at a position on the membrane surface such that its side will just abut the perimeter of the final nanopore, as shown for the side-abutting nanotube in Example II. Referring to FIGS. 11I-J, in a next process step, a layer of material 265 is deposited, e.g., by ALD, to coat all of the exposed membrane structures and to reduce the aperture to a final desired nanopore size of, e.g., between about 2 nm and about 10 nm in diameter.

Because it is difficult to manually position the end of the nanotube 260 such that its end precisely abuts on the perimeter of the final nanopore, it may be preferable to initially position the second nanotube 260 so that its end protrudes well into and across the diameter of aperture 242. Because this protruding nanotube end 262 will remain unprotected by the newly deposited ALD material when the final nanopore diameter is produced by ALD, it can be removed with an electron beam, ion beam, or other energetic beam directed through the nanopore, from the bottom or top of the support structure. As in example I, the energetic beam removes the exposed unprotected nanotube material from the nanopore, while the aluminum oxide or other ALD coating protects the ALD covered regions of the nanotubes and support structure from the beam species.

Figure 11M:
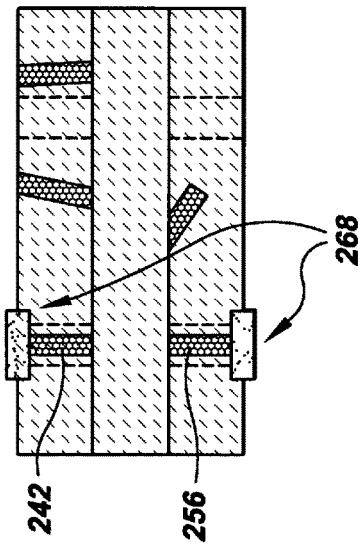
Figure 11K:
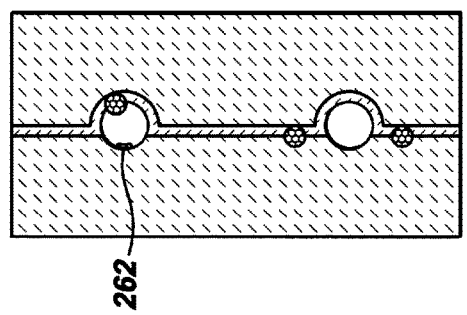
Figure 11L:
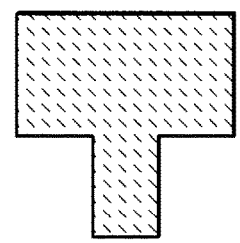
Figure 11I:
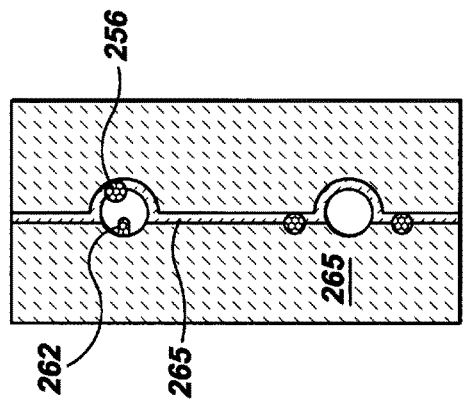
Figure 11J:
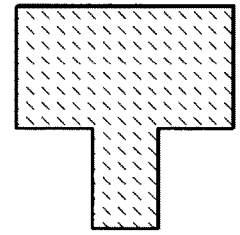

Referring also to FIG. 11M, showing a left-side end face view of the membrane structure, it can be preferred to provide metal contact pads on the ends of the vertical nanotube 256 in the nanopore 242 prior to the material deposition shown in FIGS. 11I-11L. Such metal contact regions protect the ends of the vertical nanotube 256 from being covered by the material being deposited and put metal connections in place. With the material deposition complete, a molecular characterization device like that of FIG. 4B is produced, having a first nanotube probe vertically oriented through the length of a nanopore and a second end-oriented nanotube probe.

These fabrication examples demonstrate the wide range of processes that can be employed to produce many alternative molecular characterization device configurations. The invention does not require a specific fabrication process, however; any suitable manufacturing process for producing a desired molecular characterization device arrangement can be employed.

With this discussion, it is shown that the nanopore-based molecular characterization instrument of the invention can be applied to a range of molecular characterization applications. The molecular characterization device can satisfy the requirements for a $1,000/mammalian genome assay because the instrument can directly transduce a sequence of DNA bases into an electrical signal, on the basis of their distinct physical and electrical properties, and because the instrument enables a single-molecule analysis technique that can achieve about 7.7-fold sequence coverage, or about 6.5-fold coverage in Q20 bases, and over sampling with DNA from <$10^6$ target genomes. This corresponds to about 2 nanograms of human genomic material, which can be directly obtained without amplification using standard sampling methods. If the identity of each DNA nucleoside base in a sequence of bases is resolved as the bases pass through a nanopore at a rate of about $10^4$ bases/second, then an instrument with an array of 100 such nanopores can produce a high-quality draft sequence of one mammalian genome in about 20 hours.

Thus, the high throughput and spatial confinement enabled by the nanopore configuration, in combination with the direct electronic analysis, molecular orientation control, and molecular translocation speed control enabled by a nanotube probe configuration, provide for a high-bandwidth molecular characterization process that achieves the rapid, reliable, and inexpensive molecular analysis and characterization required for a wide range of biological and medical applications. It is recognized that those skilled in the art may make various modifications and additions to the embodiments described above without departing from the spirit and scope of the present contribution to the art. Accordingly, it is to be understood that the protection sought to be afforded hereby should be deemed to extend to the subject matter claims and all equivalents thereof fairly within the scope of the invention.

We claim:

1. A molecular characterization device comprising:
   a solid state support structure including an aperture having a molecular entrance and a molecular exit;
   a first reservoir in fluidic communication with the molecular entrance of the aperture and containing a molecule-bearing liquid solution;
   a second reservoir in fluidic communication with the molecular exit of the aperture for containing a molecule-bearing liquid solution;
   a first liquid channel connected to the first reservoir within less than about 300 microns of the aperture in the solid state support structure, the first liquid channel including the molecule-bearing liquid solution for delivery to the first reservoir;
   a second liquid channel connected to the second reservoir for accepting the molecule-bearing liquid solution from the second reservoir; and
   an electrical connection between the first reservoir and the second reservoir that imposes an electrical bias between the first reservoir and the second reservoir for driving the molecule-bearing liquid solution through the aperture in the solid state support structure.

2. The molecular characterization device of claim 1 wherein the first liquid channel and the second liquid channel each having a diameter less than about 200 microns.

3. The molecular characterization device of claim 1 further comprising:
   a first tube connected to the first liquid channel for supplying the molecule-bearing liquid solution to the first liquid channel;
   a second tube connected to the second liquid channel for accepting the molecule-bearing liquid solution from the second liquid channel; and
   wherein the first tube and the second tube each have a diameter less than about 200 microns.

4. The molecular characterization device of claim 1 wherein the molecular entrance of fluidic communication between the first reservoir and the solid state support structure is less than 1000 $\mu m^2$ in area.

5. The molecular characterization device of claim 1 wherein the molecule to be characterized comprises a biomolecule.

6. The molecular characterization device of claim 1 wherein the molecule comprises a polymer molecule.

7. The molecular characterization device of claim 1 wherein the molecule comprises a biopolymer molecule.

8. The molecular characterization device of claim 7 wherein the molecule is selected from the group consisting of proteins, polynucleic acids, DNA, and RNA.

9. The molecular characterization device of claim 1 wherein the aperture comprises a pore, extending through the thickness of the support structure, and having a diameter permitting only a single molecule at a time to move through the pore.

10. The molecular characterization device of claim 1 wherein the aperture has a diameter less than about 100 nm.

11. The molecular characterization device of claim 1 wherein the aperture has a diameter less than about 10 nm.

12. The molecular characterization device of claim 1 wherein the aperture is coated with an electrically insulating material layer.

13. The molecular characterization device of claim 1 wherein the support structure comprises an electrically insulating membrane in which the aperture is provided.

14. The molecular characterization device of claim 1 wherein the aperture has a length, through a thickness of the solid state support structure between the molecular entrance and the molecular exit, that is between about 0.1 nm and about 800 nm.

* * * * *